(12) United States Patent
Schweich, Jr. et al.

(10) Patent No.: US 10,080,656 B2
(45) Date of Patent: *Sep. 25, 2018

(54) HEART VALVE ASSEMBLY SYSTEMS AND METHODS

(71) Applicant: Caisson Interventional, LLC, Maple Grove, MN (US)

(72) Inventors: Cyril J. Schweich, Jr., Maple Grove, MN (US); Todd J. Mortier, Mound, MN (US)

(73) Assignee: Caisson Interventional LLC, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/378,737

(22) Filed: Dec. 14, 2016

(65) Prior Publication Data

US 2017/0095327 A1 Apr. 6, 2017

Related U.S. Application Data

(63) Continuation of application No. 14/677,665, filed on Apr. 2, 2015, now Pat. No. 9,566,152, which is a continuation of application No. 13/842,490, filed on Mar. 15, 2013, now Pat. No. 9,011,515.

(60) Provisional application No. 61/669,383, filed on Jul. 9, 2012, provisional application No. 61/635,741, filed on Apr. 19, 2012.

(51) Int. Cl.
*A61F 2/24* (2006.01)

(52) U.S. Cl.
CPC .............. *A61F 2/2418* (2013.01); *A61F 2/24* (2013.01); *A61F 2/243* (2013.01); *A61F 2/246* (2013.01); *A61F 2/2409* (2013.01); *A61F 2/2412* (2013.01); *A61F 2/2445* (2013.01); *A61F 2/2466* (2013.01); *A61F 2220/0008* (2013.01); *A61F 2220/0016* (2013.01); *A61F 2250/006* (2013.01); *A61F 2250/0069* (2013.01); *F04C 2270/041* (2013.01)

(58) Field of Classification Search
CPC .......... A61F 2/24; A61F 2/2409; A61F 2/243; A61F 2/2412; A61F 2/2418; A61F 2/2445
See application file for complete search history.

(56) References Cited

U.S. PATENT DOCUMENTS

| | | |
|---|---|---|
| 4,680,031 A | 7/1987 | Alonso |
| 5,423,887 A | 6/1995 | Love et al. |
| 5,662,704 A | 9/1997 | Gross |
| 5,855,601 A | 1/1999 | Bessler et al. |
| 5,984,959 A | 11/1999 | Robertson et al. |

(Continued)

FOREIGN PATENT DOCUMENTS

| | | |
|---|---|---|
| EP | 350302 | 1/1990 |
| EP | 0592410 | 4/1994 |

(Continued)

OTHER PUBLICATIONS

US 9,532,869, 01/2017, Quadri et al. (withdrawn)

(Continued)

*Primary Examiner* — Alvin Stewart
(74) *Attorney, Agent, or Firm* — Fish & Richardson P.C.

(57) ABSTRACT

Heart valve assembly systems and methods configured for medical interventional procedures. In one aspect, the methods and systems involve a modular approach to treatment.

20 Claims, 12 Drawing Sheets

(56) References Cited

U.S. PATENT DOCUMENTS

| | | | |
|---|---|---|---|
| 6,113,631 A | 9/2000 | Jansen | |
| 6,296,662 B1 | 10/2001 | Caffey | |
| 6,309,417 B1 | 10/2001 | Spence et al. | |
| 6,332,893 B1 | 12/2001 | Mortier et al. | |
| 6,358,277 B1 | 3/2002 | Duran | |
| 6,425,916 B1 | 7/2002 | Garrison et al. | |
| 6,530,952 B2 | 3/2003 | Vesely | |
| 6,569,196 B1 | 5/2003 | Vesely | |
| 6,582,462 B1 | 6/2003 | Andersen et al. | |
| 6,629,534 B1 | 10/2003 | St. Goar et al. | |
| 6,730,118 B2 | 5/2004 | Spenser et al. | |
| 6,730,121 B2 | 5/2004 | Ortiz et al. | |
| 6,767,362 B2 | 7/2004 | Schreck | |
| 6,769,434 B2 | 8/2004 | Liddicoat et al. | |
| 6,790,229 B1 | 9/2004 | Berreklouw | |
| 6,883,522 B2 | 4/2005 | Spence et al. | |
| 6,893,459 B1 | 5/2005 | Macoviak | |
| 6,893,460 B2 | 5/2005 | Spenser et al. | |
| 6,908,481 B2 | 6/2005 | Cribier | |
| 6,949,122 B2 | 9/2005 | Adams et al. | |
| 7,011,681 B2 | 3/2006 | Vesely | |
| 7,018,406 B2 | 3/2006 | Seguin et al. | |
| 7,044,966 B2 | 5/2006 | Svanidze et al. | |
| 7,101,396 B2 | 9/2006 | Artof et al. | |
| 7,147,663 B1 | 12/2006 | Berg et al. | |
| 7,160,322 B2 | 1/2007 | Gabbay | |
| 7,175,656 B2 | 2/2007 | Khairkhahan | |
| 7,217,287 B2 | 5/2007 | Wilson et al. | |
| 7,252,682 B2 | 8/2007 | Seguin | |
| 7,320,704 B2 | 1/2008 | Lashinski et al. | |
| 7,329,278 B2 | 2/2008 | Seguin et al. | |
| 7,381,218 B2 | 6/2008 | Schreck | |
| 7,381,220 B2 | 6/2008 | Macoviak et al. | |
| 7,393,360 B2 | 7/2008 | Spenser et al. | |
| 7,442,204 B2 | 10/2008 | Schwammenthal et al. | |
| 7,503,930 B2 | 3/2009 | Sharkawy et al. | |
| 7,510,575 B2 | 3/2009 | Spenser et al. | |
| 7,524,330 B2 | 4/2009 | Berreklouw | |
| 7,524,331 B2 | 4/2009 | Birdsall | |
| 7,578,843 B2 | 8/2009 | Shu | |
| 7,585,321 B2 | 9/2009 | Cribier | |
| 7,597,711 B2 | 10/2009 | Drews et al. | |
| 7,618,446 B2 | 11/2009 | Andersen et al. | |
| 7,625,403 B2 | 12/2009 | Krivoruchko | |
| 7,632,308 B2 | 12/2009 | Loulmet | |
| 7,708,775 B2 | 5/2010 | Rowe et al. | |
| 7,717,955 B2 | 5/2010 | Lane et al. | |
| 7,722,666 B2 | 5/2010 | Lafontaine | |
| 7,727,276 B2 | 6/2010 | Machiraju | |
| 7,748,389 B2 | 7/2010 | Salahieh et al. | |
| 7,776,083 B2 | 8/2010 | Vesely | |
| 7,780,725 B2 | 8/2010 | Haug et al. | |
| 7,785,364 B2 | 8/2010 | Styrc | |
| 7,837,727 B2 | 11/2010 | Goetz et al. | |
| 7,896,915 B2 | 3/2011 | Guyenot et al. | |
| 7,914,569 B2 | 3/2011 | Nguyen et al. | |
| 7,935,144 B2 | 5/2011 | Robin et al. | |
| 7,947,072 B2 | 5/2011 | Yang et al. | |
| 7,947,075 B2 | 5/2011 | Goetz et al. | |
| 7,959,672 B2 | 6/2011 | Salahieh et al. | |
| 7,981,153 B2 | 7/2011 | Fogarty et al. | |
| 7,988,725 B2 | 8/2011 | Gross et al. | |
| 8,016,882 B2 | 9/2011 | Macoviak et al. | |
| 8,025,695 B2 | 9/2011 | Fogarty et al. | |
| 8,048,153 B2 | 11/2011 | Salahieh et al. | |
| 8,052,749 B2 | 11/2011 | Salahieh et al. | |
| 8,055,360 B2 | 11/2011 | Park et al. | |
| 8,057,540 B2 | 11/2011 | Letac et al. | |
| 8,062,355 B2 | 11/2011 | Figulla et al. | |
| 8,092,518 B2 | 1/2012 | Schreck | |
| 8,092,521 B2 | 1/2012 | Figulla et al. | |
| 8,092,524 B2 | 1/2012 | Nugent et al. | |
| 8,123,801 B2 | 2/2012 | Milo | |
| 8,133,270 B2 | 3/2012 | Kheradvar et al. | |
| 8,142,492 B2 | 3/2012 | Forster et al. | |
| 8,157,852 B2 | 4/2012 | Bloom et al. | |
| 8,157,853 B2 | 4/2012 | Laske et al. | |
| 8,163,011 B2 | 4/2012 | Rankin | |
| 8,172,898 B2 | 5/2012 | Alferness et al. | |
| 8,182,528 B2 | 5/2012 | Salahieh et al. | |
| 8,182,530 B2 | 5/2012 | Huber | |
| 8,206,437 B2 | 6/2012 | Bonhoeffer et al. | |
| 8,231,670 B2 | 7/2012 | Salahieh et al. | |
| 8,236,049 B2 | 8/2012 | Rowe et al. | |
| 8,246,677 B2 | 8/2012 | Ryan | |
| 8,252,051 B2 | 8/2012 | Chau et al. | |
| 8,262,724 B2 | 9/2012 | Seguin et al. | |
| 8,273,120 B2 | 9/2012 | Dolan | |
| 8,277,502 B2 | 10/2012 | Miller et al. | |
| 8,282,051 B2 | 10/2012 | Nutaro et al. | |
| 8,287,591 B2 | 10/2012 | Keidar et al. | |
| 8,292,938 B2 | 10/2012 | Case | |
| 8,308,796 B2 | 11/2012 | Lashinski et al. | |
| 8,308,798 B2 | 11/2012 | Pintor et al. | |
| 8,317,858 B2 | 11/2012 | Straubinger et al. | |
| 8,323,332 B2 | 12/2012 | Agnew | |
| 8,323,335 B2 | 12/2012 | Rowe et al. | |
| 8,348,998 B2 | 1/2013 | Pintor et al. | |
| 8,403,983 B2 | 3/2013 | Quadri et al. | |
| 8,449,599 B2 | 5/2013 | Chau et al. | |
| 8,454,686 B2 | 6/2013 | Alkhatib | |
| 8,460,366 B2 | 6/2013 | Rowe | |
| 8,500,798 B2 | 8/2013 | Rowe et al. | |
| 8,512,398 B2 | 8/2013 | Alkhatib | |
| 8,512,399 B2 | 8/2013 | Lafontaine | |
| 8,568,477 B2 | 10/2013 | Lashinski et al. | |
| 8,579,964 B2 | 11/2013 | Lane et al. | |
| 8,585,755 B2 | 11/2013 | Chau et al. | |
| 8,623,080 B2 | 1/2014 | Fogarty et al. | |
| 8,628,569 B2 | 1/2014 | Benichou et al. | |
| 8,628,571 B1 | 1/2014 | Hacohen et al. | |
| 8,632,586 B2 | 1/2014 | Spenser et al. | |
| 8,641,757 B2 | 2/2014 | Pintor et al. | |
| 8,652,203 B2 | 2/2014 | Quadri et al. | |
| 8,657,872 B2 | 2/2014 | Seguin | |
| 8,685,085 B2 | 4/2014 | Guyenot et al. | |
| 8,685,086 B2 | 4/2014 | Navia et al. | |
| 8,696,742 B2 | 4/2014 | Pintor et al. | |
| 8,728,155 B2 | 5/2014 | Montorfano et al. | |
| 8,795,355 B2 | 8/2014 | Alkhatib | |
| 8,795,356 B2 | 8/2014 | Quadri et al. | |
| 8,808,371 B2 | 8/2014 | Cartledge | |
| 8,834,564 B2 | 9/2014 | Tuval et al. | |
| 8,840,662 B2 | 9/2014 | Salahieh et al. | |
| 8,840,663 B2 | 9/2014 | Salahieh et al. | |
| 8,845,720 B2 | 9/2014 | Conklin | |
| 8,852,272 B2 | 10/2014 | Gross et al. | |
| 8,858,620 B2 | 10/2014 | Salahieh et al. | |
| 8,870,948 B1 | 10/2014 | Erzberger et al. | |
| 8,870,949 B2 | 10/2014 | Rowe | |
| 8,876,895 B2 | 11/2014 | Tuval et al. | |
| 8,894,702 B2 | 11/2014 | Quadri et al. | |
| 8,911,493 B2 | 12/2014 | Rowe et al. | |
| 8,926,690 B2 | 1/2015 | Kovalsky | |
| 8,926,691 B2 | 1/2015 | Chau et al. | |
| 8,932,358 B1 | 1/2015 | Nehls | |
| 8,961,595 B2 | 2/2015 | Alkhatib | |
| 8,968,395 B2 | 3/2015 | Hauser et al. | |
| 8,986,370 B2 | 3/2015 | Annest | |
| 8,986,373 B2 | 3/2015 | Chau et al. | |
| 9,005,277 B2 | 4/2015 | Pintor et al. | |
| 9,005,278 B2 | 4/2015 | Pintor et al. | |
| 9,011,515 B2 * | 4/2015 | Schweich, Jr. | A61F 2/243 623/1.26 |
| 9,017,399 B2 | 4/2015 | Gross et al. | |
| 9,023,100 B2 | 5/2015 | Quadri et al. | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,039,759 B2 | 5/2015 | Alkhatib et al. | |
| 9,050,188 B2 | 6/2015 | Schweich et al. | |
| 9,066,801 B2 | 6/2015 | Kovalsky et al. | |
| 9,072,604 B1 | 7/2015 | Melnick et al. | |
| 9,084,676 B2 | 7/2015 | Chau et al. | |

(56) References Cited

U.S. PATENT DOCUMENTS

| | | |
|---|---|---|
| 9,132,006 B2 | 9/2015 | Spenser et al. |
| 9,155,617 B2 | 10/2015 | Carpentier et al. |
| 9,168,130 B2 | 10/2015 | Straubinger |
| 9,168,133 B2 | 10/2015 | Spenser et al. |
| 9,173,738 B2 | 11/2015 | Murray, III et al. |
| 9,192,466 B2 | 11/2015 | Kovalsky et al. |
| 9,226,826 B2 | 1/2016 | Rust |
| 9,241,792 B2 | 1/2016 | Benichou et al. |
| 9,248,016 B2 | 2/2016 | Oba |
| 9,259,315 B2 | 2/2016 | Zhou et al. |
| 9,265,631 B2 | 2/2016 | Straubinger |
| 9,289,293 B2 | 3/2016 | Murad et al. |
| 9,295,547 B2 | 3/2016 | Costello et al. |
| 9,295,548 B2 | 3/2016 | Drews et al. |
| 9,295,550 B2 | 3/2016 | Nguyen et al. |
| 9,301,843 B2 | 4/2016 | Richardson et al. |
| 9,301,863 B2 | 4/2016 | Punga et al. |
| 9,331,328 B2 | 5/2016 | Eberhardt et al. |
| 9,339,377 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,345,573 B2 | 5/2016 | Nyuli et al. |
| 9,358,111 B2 | 6/2016 | Spence et al. |
| 9,370,423 B2 | 6/2016 | Ryan |
| 9,370,424 B2 | 6/2016 | Call et al. |
| 9,375,311 B2 | 6/2016 | Gloss et al. |
| 9,439,757 B2 | 6/2016 | Wallace et al. |
| 9,492,273 B2 | 6/2016 | Wallace et al. |
| 9,387,071 B2 | 7/2016 | Tuval et al. |
| 9,402,719 B2 | 8/2016 | Lane et al. |
| 9,402,721 B2 | 8/2016 | Buchbinder et al. |
| 9,414,913 B2 | 8/2016 | Beith et al. |
| 9,414,918 B2 | 8/2016 | Chau et al. |
| 9,433,503 B2 | 9/2016 | Tsukashima et al. |
| 9,456,896 B2 | 10/2016 | Quadri et al. |
| 9,468,525 B2 | 10/2016 | Kovalsky |
| 9,480,556 B2 | 11/2016 | Revuelta et al. |
| 9,480,559 B2 | 11/2016 | Vidlund et al. |
| 9,486,306 B2 | 11/2016 | Tegels et al. |
| 9,510,946 B2 | 12/2016 | Chau et al. |
| 9,522,062 B2 | 12/2016 | Tuval |
| 9,532,870 B2 | 1/2017 | Cooper et al. |
| 9,554,903 B2 | 1/2017 | Rowe et al. |
| 9,561,100 B2 | 2/2017 | Pintor et al. |
| 9,561,103 B2 | 2/2017 | Granada et al. |
| 9,566,152 B2 * | 2/2017 | Schweich, Jr. ......... A61F 2/243 |
| 9,572,662 B2 | 2/2017 | Morriss et al. |
| 9,579,194 B2 | 2/2017 | Elizondo et al. |
| 9,579,196 B2 | 2/2017 | Morriss et al. |
| 2001/0007956 A1 | 7/2001 | Letac et al. |
| 2001/0021872 A1 | 9/2001 | Bailey et al. |
| 2002/0151970 A1 | 10/2002 | Garrison et al. |
| 2003/0130726 A1 | 7/2003 | Thorpe et al. |
| 2004/0210307 A1 | 10/2004 | Khairkhahan |
| 2005/0137689 A1 | 6/2005 | Salaheih et al. |
| 2005/0137690 A1 | 6/2005 | Salahieh et al. |
| 2005/0165479 A1 | 7/2005 | Drews et al. |
| 2006/0235509 A1 | 10/2006 | Lafontaine |
| 2007/0027533 A1 | 2/2007 | Douk |
| 2007/0168024 A1 | 7/2007 | Khairkhahan |
| 2007/0185565 A1 | 8/2007 | Schwammenthal et al. |
| 2008/0004697 A1 | 1/2008 | Lichetenstein et al. |
| 2008/0015671 A1 | 1/2008 | Bonhoeffer |
| 2008/0086164 A1 | 4/2008 | Rowe |
| 2008/0103586 A1 | 5/2008 | Styrc et al. |
| 2008/0140189 A1 | 6/2008 | Nguyen et al. |
| 2008/0183273 A1 | 7/2008 | Mesana |
| 2008/0221672 A1 | 9/2008 | Lamphere et al. |
| 2009/0005863 A1 | 1/2009 | Goetz et al. |
| 2009/0216312 A1 | 8/2009 | Straubinger et al. |
| 2010/0049315 A1 | 2/2010 | Kirson |
| 2010/0100173 A1 | 4/2010 | Lafontaine |
| 2010/0217382 A1 | 8/2010 | Chau |
| 2010/0249894 A1 | 9/2010 | Oba |
| 2010/0249908 A1 | 9/2010 | Chau et al. |
| 2010/0262232 A1 | 10/2010 | Annest |
| 2010/0280606 A1 | 11/2010 | Naor |
| 2010/0298931 A1 | 11/2010 | Quadri et al. |
| 2010/0312333 A1 | 12/2010 | Navia et al. |
| 2010/0331972 A1 | 12/2010 | Pintor et al. |
| 2011/0004296 A1 | 1/2011 | Lutter et al. |
| 2011/0022168 A1 | 1/2011 | Cartledge |
| 2011/0040374 A1 | 2/2011 | Goetz et al. |
| 2011/0137397 A1 | 6/2011 | Chau et al. |
| 2011/0137410 A1 | 6/2011 | Hacohen |
| 2011/0166636 A1 | 7/2011 | Rowe |
| 2011/0208293 A1 | 8/2011 | Tabor |
| 2011/0218619 A1 | 9/2011 | Benichou et al. |
| 2011/0224785 A1 | 9/2011 | Hacohen |
| 2011/0245911 A1 | 10/2011 | Quill et al. |
| 2011/0257721 A1 | 10/2011 | Tabor |
| 2011/0282438 A1 | 11/2011 | Drews et al. |
| 2011/0295363 A1 | 12/2011 | Girard et al. |
| 2011/0301702 A1 | 12/2011 | Rust et al. |
| 2011/0319988 A1 | 12/2011 | Schankereli et al. |
| 2011/0319989 A1 | 12/2011 | Lane et al. |
| 2012/0010697 A1 | 1/2012 | Shin et al. |
| 2012/0016464 A1 | 1/2012 | Seguin |
| 2012/0035722 A1 | 2/2012 | Tuval |
| 2012/0053675 A1 | 3/2012 | Borock |
| 2012/0059458 A1 | 3/2012 | Buchbinder et al. |
| 2012/0078357 A1 | 3/2012 | Conklin |
| 2012/0101571 A1 | 4/2012 | Thambar et al. |
| 2012/0136430 A1 | 5/2012 | Sochman et al. |
| 2012/0310328 A1 | 12/2012 | Olson et al. |
| 2013/0053949 A1 | 2/2013 | Pintor et al. |
| 2013/0079869 A1 | 3/2013 | Straubinger |
| 2013/0090725 A1 | 4/2013 | Pintor et al. |
| 2013/0116777 A1 | 5/2013 | Pintor et al. |
| 2013/0172992 A1 | 7/2013 | Gross et al. |
| 2013/0184811 A1 | 7/2013 | Rowe et al. |
| 2013/0190861 A1 | 7/2013 | Chau et al. |
| 2013/0211508 A1 | 8/2013 | Lane et al. |
| 2013/0282110 A1 | 10/2013 | Schweich et al. |
| 2013/0282114 A1 | 10/2013 | Schweich et al. |
| 2013/0304200 A1 | 11/2013 | McLean et al. |
| 2013/0345799 A1 | 12/2013 | Lafontaine |
| 2014/0005778 A1 | 1/2014 | Buchbinder et al. |
| 2014/0012368 A1 | 1/2014 | Sugimoto |
| 2014/0012372 A1 | 1/2014 | Chau et al. |
| 2014/0012373 A1 | 1/2014 | Chau et al. |
| 2014/0039611 A1 | 2/2014 | Lane et al. |
| 2014/0052237 A1 | 2/2014 | Lane et al. |
| 2014/0214156 A1 | 7/2014 | Navia et al. |
| 2014/0222136 A1 | 8/2014 | Geist et al. |
| 2014/0228946 A1 | 8/2014 | Chau et al. |
| 2014/0236291 A1 | 8/2014 | Schweich et al. |
| 2014/0257467 A1 | 9/2014 | Lane et al. |
| 2014/0316516 A1 | 10/2014 | Vidlund |
| 2014/0343669 A1 | 11/2014 | Lane et al. |
| 2014/0358223 A1 | 12/2014 | Rafiee et al. |
| 2014/0364943 A1 | 12/2014 | Conklin |
| 2015/0039083 A1 | 2/2015 | Rafiee |
| 2015/0094802 A1 | 4/2015 | Buchbinder et al. |
| 2015/0112433 A1 | 4/2015 | Schweich et al. |
| 2015/0127096 A1 | 5/2015 | Rowe et al. |
| 2015/0142103 A1 | 5/2015 | Vidlund |
| 2015/0150678 A1 | 6/2015 | Brecker |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0216656 A1 | 8/2015 | Pintor et al. |
| 2015/0216657 A1 | 8/2015 | Braido |
| 2015/0216658 A1 | 8/2015 | Braido |
| 2015/0216660 A1 | 8/2015 | Pintor et al. |
| 2015/0238312 A1 | 8/2015 | Lashinski |
| 2015/0238313 A1 | 8/2015 | Spence et al. |
| 2015/0265402 A1 | 9/2015 | Centola et al. |
| 2015/0320553 A1 | 11/2015 | Chau et al. |
| 2015/0327995 A1 | 11/2015 | Morin et al. |
| 2015/0327996 A1 | 11/2015 | Fahim et al. |
| 2015/0327999 A1 | 11/2015 | Board et al. |

(56) References Cited

U.S. PATENT DOCUMENTS

| | | |
|---|---|---|
| 2015/0335421 A1 | 11/2015 | Figulla et al. |
| 2015/0342733 A1 | 12/2015 | Alkhatib et al. |
| 2015/0351906 A1 | 12/2015 | Hammer et al. |
| 2015/0359629 A1 | 12/2015 | Ganesan et al. |
| 2016/0000564 A1 | 1/2016 | Buchbinder et al. |
| 2016/0008131 A1 | 1/2016 | Christianson et al. |
| 2016/0022417 A1 | 1/2016 | Karapetian et al. |
| 2016/0045307 A1 | 2/2016 | Yohanan et al. |
| 2016/0045309 A1 | 2/2016 | Valdez et al. |
| 2016/0051362 A1 | 2/2016 | Cooper et al. |
| 2016/0074160 A1 | 3/2016 | Christianson et al. |
| 2016/0106539 A1 | 4/2016 | Buchbinder et al. |
| 2016/0120646 A1 | 5/2016 | Dwork et al. |
| 2016/0158000 A1 | 6/2016 | Granada et al. |
| 2016/0158001 A1 | 6/2016 | Wallace et al. |
| 2016/0158003 A1 | 6/2016 | Wallce et al. |
| 2016/0184095 A1 | 6/2016 | Spence et al. |
| 2016/0193044 A1 | 7/2016 | Achiluzzi |
| 2016/0199180 A1 | 7/2016 | Zeng et al. |
| 2016/0220364 A1 | 8/2016 | Straubinger |
| 2016/0228251 A1 | 8/2016 | Nyuli et al. |
| 2016/0235529 A1 | 8/2016 | Ma et al. |
| 2016/0242906 A1 | 8/2016 | Morriss et al. |
| 2016/0270917 A1 | 9/2016 | Tuval et al. |
| 2016/0310268 A1 | 10/2016 | Oba et al. |
| 2016/0317290 A1 | 11/2016 | Chau et al. |
| 2016/0317304 A1 | 11/2016 | Spence et al. |
| 2016/0324631 A1 | 11/2016 | Lane et al. |
| 2016/0324633 A1 | 11/2016 | Gross et al. |
| 2016/0331523 A1 | 11/2016 | Chau et al. |
| 2016/0331531 A1 | 11/2016 | Quadri et al. |
| 2016/0331534 A1 | 11/2016 | Buchbinder et al. |
| 2016/0338826 A1 | 11/2016 | Chau et al. |
| 2016/0338829 A1 | 11/2016 | Call et al. |
| 2016/0346080 A1 | 12/2016 | Righini et al. |
| 2016/0354203 A1 | 12/2016 | Tuval et al. |
| 2016/0354204 A1 | 12/2016 | Braido et al. |
| 2016/0361162 A1 | 12/2016 | Richter et al. |
| 2016/0361163 A1 | 12/2016 | Yohanan et al. |
| 2016/0374801 A1 | 12/2016 | Jiminez et al. |
| 2017/0007398 A1 | 1/2017 | Drews et al. |
| 2017/0049564 A1 | 2/2017 | Board et al. |
| 2017/0056162 A1 | 3/2017 | Harewood |
| 2017/0056163 A1 | 3/2017 | Tayeb et al. |
| 2017/0056166 A1 | 3/2017 | Ratz et al. |
| 2017/0056176 A1 | 3/2017 | Rowe et al. |

FOREIGN PATENT DOCUMENTS

| | | |
|---|---|---|
| EP | 592410 | 4/1994 |
| EP | 705081 | 10/2001 |
| EP | 1338255 | 8/2003 |
| EP | 825841 | 10/2003 |
| EP | 833595 | 10/2003 |
| EP | 910313 | 11/2003 |
| EP | 910314 | 11/2003 |
| EP | 0910314 | 11/2003 |
| EP | 1006949 | 10/2004 |
| EP | 1233731 | 12/2004 |
| EP | 1251803 | 6/2005 |
| EP | 2674130 | 6/2005 |
| EP | 1267753 | 10/2005 |
| EP | 830112 | 11/2005 |
| EP | 1171059 | 11/2005 |
| EP | 1328215 | 11/2005 |
| EP | 1318775 | 11/2006 |
| EP | 1474077 | 2/2007 |
| EP | 1143882 | 12/2007 |
| EP | 1180987 | 8/2008 |
| EP | 1237509 | 12/2008 |
| EP | 1562522 | 12/2008 |
| EP | 2000115 | 12/2008 |
| EP | 1330213 | 3/2009 |
| EP | 1610727 | 4/2009 |
| EP | 1343438 | 7/2009 |
| EP | 2078498 | 7/2009 |
| EP | 1684667 | 8/2009 |
| EP | 1408850 | 9/2009 |
| EP | 1653888 | 9/2009 |
| EP | 1049425 | 11/2009 |
| EP | 1703865 | 2/2010 |
| EP | 1682048 | 3/2010 |
| EP | 1509171 | 6/2010 |
| EP | 1968491 | 7/2010 |
| EP | 1176913 | 10/2010 |
| EP | 1465554 | 12/2010 |
| EP | 1940321 | 12/2010 |
| EP | 2258312 | 12/2010 |
| EP | 1441672 | 9/2011 |
| EP | 2160150 | 10/2011 |
| EP | 1603493 | 12/2011 |
| EP | 2399549 | 12/2011 |
| EP | 2399550 | 12/2011 |
| EP | 1788984 | 2/2012 |
| EP | 2055266 | 2/2012 |
| EP | 2420205 | 2/2012 |
| EP | 1621162 | 5/2012 |
| EP | 2138132 | 6/2012 |
| EP | 2476394 | 7/2012 |
| EP | 2124824 | 10/2012 |
| EP | 2088965 | 11/2012 |
| EP | 2526895 | 11/2012 |
| EP | 2526898 | 11/2012 |
| EP | 2526899 | 11/2012 |
| EP | 2529696 | 12/2012 |
| EP | 2529697 | 12/2012 |
| EP | 2529698 | 12/2012 |
| EP | 2529699 | 12/2012 |
| EP | 2537487 | 12/2012 |
| EP | 1919397 | 1/2013 |
| EP | 2015709 | 1/2013 |
| EP | 1750622 | 2/2013 |
| EP | 2257242 | 2/2013 |
| EP | 2260796 | 2/2013 |
| EP | 1701668 | 3/2013 |
| EP | 2260797 | 3/2013 |
| EP | 2340075 | 3/2013 |
| EP | 2260798 | 6/2013 |
| EP | 2626040 | 8/2013 |
| EP | 1758523 | 9/2013 |
| EP | 2073756 | 10/2013 |
| EP | 2109417 | 11/2013 |
| EP | 2477555 | 12/2013 |
| EP | 1838241 | 2/2014 |
| EP | 1926455 | 4/2014 |
| EP | 2405966 | 4/2014 |
| EP | 2257243 | 5/2014 |
| EP | 2316381 | 5/2014 |
| EP | 2745805 | 6/2014 |
| EP | 2117469 | 7/2014 |
| EP | 2124826 | 7/2014 |
| EP | 2258316 | 7/2014 |
| EP | 2749254 | 7/2014 |
| EP | 1667604 | 8/2014 |
| EP | 2211779 | 8/2014 |
| EP | 2772228 | 9/2014 |
| EP | 2142143 | 11/2014 |
| EP | 2815723 | 12/2014 |
| EP | 2815724 | 12/2014 |
| EP | 2815725 | 12/2014 |
| EP | 2254515 | 1/2015 |
| EP | 1465555 | 5/2015 |
| EP | 2068767 | 7/2015 |
| EP | 1702247 | 8/2015 |
| EP | 1729688 | 8/2015 |
| EP | 2262447 | 8/2015 |
| EP | 2901966 | 8/2015 |
| EP | 1804686 | 9/2015 |
| EP | 2675396 | 9/2015 |
| EP | 1734903 | 10/2015 |
| EP | 2254513 | 10/2015 |
| EP | 2544626 | 10/2015 |
| EP | 2926766 | 10/2015 |
| EP | 2926767 | 10/2015 |

(56) References Cited

FOREIGN PATENT DOCUMENTS

| | | |
|---|---|---|
| EP | 1748745 | 12/2015 |
| EP | 1755459 | 12/2015 |
| EP | 1850796 | 12/2015 |
| EP | 1991168 | 1/2016 |
| EP | 2254512 | 1/2016 |
| EP | 2263609 | 1/2016 |
| EP | 2012712 | 2/2016 |
| EP | 1585463 | 3/2016 |
| EP | 2170416 | 3/2016 |
| EP | 2278944 | 3/2016 |
| EP | 1871300 | 4/2016 |
| EP | 2572676 | 4/2016 |
| EP | 2626041 | 4/2016 |
| EP | 2237746 | 5/2016 |
| EP | 2582326 | 5/2016 |
| EP | 2618784 | 5/2016 |
| EP | 1734902 | 6/2016 |
| EP | 1906884 | 6/2016 |
| EP | 2190379 | 6/2016 |
| EP | 2416739 | 6/2016 |
| EP | 2572675 | 6/2016 |
| WO | WO 2007/100410 | 9/2007 |
| WO | WO 2011/119101 | 9/2011 |
| WO | WO 2012/103204 | 8/2012 |
| WO | WO 2013/114214 | 8/2013 |

OTHER PUBLICATIONS

International Preliminary Report on Patentability in International Application No. PCT/US2015/035303, dated Dec. 15, 2016, 10 pages.
U.S. Appl. No. 61/266,774, filed Dec. 16, 2009, Chau et al.
U.S. Appl. No. 61/287,099, filed Dec. 4, 2009, Chau et al.
Extended European Search Report in European Application No. 13778799.0, dated Dec. 21, 2015, 7 pages.
International Preliminary Report on Patentability in International Application No. PCT/US2013/036734, dated Oct. 21, 2014, 9 pages.
International Search Report and Written Opinion in Application No. PCT/US2013/036728, dated Aug. 8, 2013, 3 pages.
International Search Report and Written Opinion in Application No. PCT/US2013/036734, dated Aug. 20, 2013, 4 pages.
International Search Report and Written Opinion in International Application No. PCT/US2015/056935, dated Feb. 12, 2016, 13 pages.
Supplementary European Search Report in European Application No. 13778768, dated Jan. 12, 2016, 7 pages.

* cited by examiner

HEART VALVE ASSEMBLY SYSTEMS AND METHODS

CROSS-REFERENCES TO RELATED APPLICATIONS

This document is a continuation of U.S. application Ser. No. 14/677,665 filed on Apr. 2, 2015, which is a continuation of U.S. application Ser. No. 13/842,490 filed on Mar. 15, 2013, which claims the benefit of: U.S. Provisional Application Ser. No. 61/635,741 filed on Apr. 19, 2012, and U.S. Provisional Application Ser. No. 61/669,383 filed on Jul. 9, 2012, the entire disclosures of these previous applications being expressly incorporated herein.

BACKGROUND OF THE DISCLOSURE

The present disclosure relates to medical interventional systems and methods and more particularly, to artificial valve assembly systems and methods. The long-term clinical effect of valve regurgitation is well recognized as a significant contributor to cardiovascular related morbidity and mortality. In particular, there are two basic classifications of mitral regurgitation ("MR"), primary and secondary. Primary MR results when there is either direct tissue pathology of the valve structures or there is structural damage/alteration of one or more valve structures (leaflets, chordae). Secondary MR is a functional loss of valve competence caused left ventricular dilatation, and secondary alteration of mitral valve geometry following damage to the myocardium and left ventricle ("LV") causing. Whether valvular in origin leading to a ventricular problem or of ventricular/muscle origin leading to the valvular problem, the effect of high levels of MR is significant on cardiopulmonary physiology, resulting in significantly elevated left atrial pressures and pulmonary pressures, pulmonary congestion, and volume and energy overload effects on the myocardium. This physiology creates significant heart failure symptoms of shortness of breath and decreased physical endurance, ultimately leading to death.

The decision to intervene on a regurgitant mitral valve relates to the level of mitral regurgitation, the symptoms of the patient as an indicator of progressive negative physiologic effect, and the functional status of the left ventricle, specifically ejection fraction. The risk of intervention is weighed against the benefit of MR treatment.

The mitral valve is a therapeutic target of intervention/surgery early in the disease process of primary valvular disease because of MR's deleterious effects on heart/ventricular function if left untreated. For patients with moderate-severe or severe levels of MR combined with even a modest decrease in ejection fraction ("EF"), or the development of symptoms, surgical correction is indicated. In this situation, the risk of surgery in what is an otherwise healthy patient is far outweighed by the beneficial effects of eliminating the long-term negative effects of MR.

A more difficult question has been the patient with secondary or functional mitral regurgitation. In this situation, the patient has pre-existing LV dysfunction combined with heart failure symptoms, and a developing/worsening level of MR. The risks of intervention in this scenario are much greater. The net benefit of surgically intervening to eliminate the MR has not been demonstrated. Symptomatic benefit has been seen, but not a net mortality benefit. Therefore, it is usually contemplated or applied concomitantly when a patient is undergoing coronary artery bypass graft CABG revascularization.

The classification of mitral regurgitation as primary or secondary is a useful to differentiate between the underlying disease processes that led to the incompetent valve. These provide a starting point that can direct the type and timing of an intervention. However, it is not sufficient to fully describe the issues that direct a therapeutic approach. Because the mitral valve is complex structurally, mechanically, and physiologically, a more detailed description and understanding of the abnormalities associated with mitral regurgitation is needed to direct existing therapies, as well as develop new options for therapy.

Pathologic abnormality of the mitral valve tissue is a common cause of primary mitral regurgitation. Typical pathologies that occur include rheumatic, myxomatous, endocarditis, and Marfan's or other collagen based tissue diseases. Calcification and leaflet thickening are also abnormalities associated with direct tissue level changes in the valve. These can be either part of a primary tissue based disease or result from a long-standing insult to the valve, including regurgitant jetting across the leaflets.

Congenital and acquired structural abnormalities like ruptured chordae, leaflet prolapse, fenestrations, and clefts can also be forms of primary valve disease leading to mitral regurgitation.

Functional MR results from myocardial damage leading to ventricular functional loss and geometric changes that impact the valve coaptation through associated annular dilatation and papillary muscle displacement. In pure functional MR, the valve structures are not pathologic nor have structural defects, but the geometric alteration leads to a loss of coaptation of the mitral valve leaflets, often in the central A2/P2 segment of the valve.

As with many multi-factorial clinical problems, one etiologic element (tissue pathology, structural alterations, functional/geometric changes) may lead to others resulting in a "mixed" picture. This is especially true with mitral regurgitation. In the case of primary MR of either tissue or structural origin, volume overload of the LV can create failure and LV dilatation creating a component of functional MR if the valve is left untreated. In the case of long standing functional MR, tissue changes can be seen such as calcification and thickening caused by the regurgitant jet and high leaflet stresses. Muscle/tissue damage to the myocardium in and around the sub-valvular apparatus can create structural alteration such as ruptured papillary muscles/chordae and prolapse. Excessive tenting of the leaflets associated with significant functional MR can also stress the chords causing rupture.

The net result is that MR is a spectrum disorder with many patients having a mixed picture of valve abnormalities. This is an important factor in the decisions surrounding a mitral valve therapeutic approach, specifically repair or replacement.

The primary goal of any therapy of the mitral valve is to significantly reduce or eliminate the regurgitation. By eliminating the regurgitation, the destructive volume overload effects on the left ventricle are attenuated. The volume overload of regurgitation relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumic contraction. Additionally, successful MR reduction should have the effect of reducing the elevated pressures in the left atrium and pulmonary vasculature reducing pulmonary edema (congestion) and shortness of breath symptomatology. It also has a positive effect on the filling profile of the left ventricle and the restrictive LV physiology that can result with MR. These pathophysiologic issues indicate the potential benefits of MR therapy, but also indicates the complexity of the system and the need for a therapy to focus beyond the MR level or grade.

It is also desirable to prevent new deleterious physiology or function of the valve. The procedure and system used to fix the mitral valve needs to avoid worsening other (non-MR) existing pathologic conditions or creating new pathologic conditions as a result of the treatment of the critical factors to be managed is Stenosis/gradient. That is, if a valve system is used that does not allow for sufficient LV inflow without elevated filling pressures, then critical benefits of MR reduction are dissipated or lost. Moreover, Atrial fibrillation is to be avoided as it can result if elevated pressures are not relieved by the therapy, or are created by the system (high pressure results in atrial stress leading to dilatation ultimately leading to arrhythmias). Also, if the procedure results in damage to atrial tissue at surgery it can result in the negative physiologic effect of atrial fibrillation. Further, one should be aware of the possibility of increased LV Wall Stress (LV geometry). Due to the integral relationship of the mitral valve with LV geometry through the papillary and chordal apparatus, LV wall stress levels can be directly affected resulting in alterations of LV filling and contraction mechanics. Accordingly, a system that does not preserve or worsens the geometry of the LV can counter the benefits of MR reduction because of the alteration of contractile physiology.

It has been generally agreed that it is preferable if the valve can be repaired. Repair of valve elements that target the regurgitant jet only allows for minimal alteration to the valve elements/structures that are properly functioning allowing for the least potential for negatively effecting the overall physiology while achieving the primary goal. Native valve preservation can be beneficial because a well repaired valve is considered to have a better chance of having long standing durability versus a replacement with an artificial valve that has durability limits. Also, while current surgical artificial valves attempt chord sparing procedures, the LV geometric relationship may be negatively altered if not performed or performed poorly leading to an increase in LV wall stress due to an increase in LV diameter. Thus, while preferred and possible for technically competent surgeons, the relatively high recurrence rate of MR due to inadequate repair, the invasiveness of the surgery especially in sick or functional MR patients, and the complexities of a repair for many surgeons lead to a high percentage of mitral operations being replacement.

Conventionally, surgical repair or replacement of the mitral valve is performed on cardiopulmonary bypass and is usually performed via an open median sternotomy resulting in one of the most invasive high risk cardiac surgical operations performed, especially in subpopulations such as functional MR. Therefore, a key improvement to mitral valve operations is to significantly lower the risk and invasiveness, specifically utilizing a percutaneous or minimally invasive technique.

While there have been attempts to replicate existing surgical repair via less invasive surgical or percutaneous methods, given the complexity of repairing the valve surgically, the efforts have largely been deemed lacking adequate efficacy and have not altered the risk benefit ratio sufficiently to warrant ongoing investment, approval, or adoption. In particular, there has been a general technology failure due to the complexity of anatomy to percutaneously manage with an implant or implantable procedure. The broad spectrum of mitral disease directly influences outcomes with a resulting inability to match technology with pathology. There has also been observed inadequate efficacy with poor surgical replication and safety results. It has also been recognized that percutaneous approaches successful to certain valve procedures such as aortic valve replacement associated with a single pathology and a relatively circular rigid substrate, mitral valves often suffer from multiple pathologies and a flexible or elastic annular with multiple structures.

Accordingly, what is needed is an effective long lasting MR reduction without creating negative physiologic consequences to the cardio-pulmonary system (heart, lungs, peripheral vasculature) including stenosis, LV wall stress and atrial fibrillation. It is also desirable to be able to perform the operation in a reliable, repeatable, and easy to perform procedure and to have a broadly applicable procedure for both patients and physicians, while employing a significantly less invasive method.

The present disclosure addresses these and other needs.

SUMMARY

Briefly and in general terms, the present disclosure is directed towards heart valve assembly systems and methods. In one particular aspect, the present disclosure presents various approaches to heart valve assembly systems configured to eliminate MR, provide adequate physiologic inflow, and preserve and/or improve LV geometry.

In one aspect, there is provided a heart valve assembly system for implantation at an interventional site including an anchor and a valve assembly defining structure configured to treat a native heart, and a method for implanting the same.

In other aspects, there is provided a heart valve assembly system for implantation at an interventional site which includes an anchor, the anchor including structure residing above and below a valve annulus and an interior and a valve assembly defining structure configured to be implanted separately from the anchor and having an exterior sized and shaped to lockingly engage the interior of the anchor. In further aspects, the valve assembly can include a plurality of annular ridges shaped to lockingly receive the anchor, or a generally cylindrical portion and a tapered portion extending from the generally cylindrical portion, the tapered portion contoured to mate with native valve anatomy. The valve assembly can additionally include a surface configured for tissue ingrowth, a projecting member extending beyond the tapered portion, the projecting member sized and shaped to engage native valve anatomy to offset rotational forces, and/or a tapered section extending within heart anatomy to engage a wall in a heart chamber. Moreover, the valve assembly can be configured to present structure which is at an angle with respect to a native valve opening, and define structure supporting five or more leaflets. The valve assembly can also include leaflets which include non-coaptive tips which extend below the native valve leaflets, a laterally arranged tri-leaflet arrangement, and/or leaflets which open and close in response to functioning of native leaflets, or which define a tubular structure with a wall that collapses to close the valve assembly. In yet another aspect, the valve assembly can include flap-like leaflets certain of which can be arranged at different angles from other flap-like leaflets.

In various approaches, a heart valve assembly system and method addresses a number of basic functional requirements. One requirement is the valve function itself, the occlusion of flow during systole, and open to flow during diastole. Another requirement is the seal between the artificial replacement valve frame/structure and the tissue to prevent/minimize any peri-valvular leaks or flow. A further requirement is the anchoring or securement function to hold the functioning valve in position and withstand the substantial and variable cyclical load placed on the valve during systolic pressurization of the valve surface. It is intended that each of these is met in the durable, therapeutically, and physiologically appropriate valve replacement system disclosed herein.

A valve replacement system according to the present disclosure includes a valve element and a valve delivery system. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary.

A valve to anchor interface can involve a geometric interlock, to thereby allow the flexibility for adaptation to a broad spectrum of valve technology. In this regard, a valve to native valve interface preserves sub-valvular structure relationships.

Further, design and delivery approaches that maintain native valve function providing the ability to completely separate and stage the implantation of the system functional components is contemplated as are delivery methods that have potential for quick fluoroscopic delivery, positioning, and deployment. Consequently, there is an optimal valve performance opportunity due to maximal design flexibility and a delivery capability to achieve precise positioning. The same creates desired tissue/implant seating and maintains sub-valvular structural relationships.

Accordingly, employing the present system facilitates effective long lasting MR reduction without creating negative physiologic consequences to the cardio-pulmonary system (heart, lungs, peripheral vasculature) including stenosis, LV wall stress, and atrial fibrillation. The system facilitates a reliable and a broadly applicable approach for both patients and physicians.

Other features and advantages of the present disclosure will become apparent from the following detailed description, taken in conjunction with the accompanying drawings, which illustrate, by way of example, the principles of the invention.

DETAILED DESCRIPTION OF THE PREFERRED EMBODIMENTS

Figure 1A:
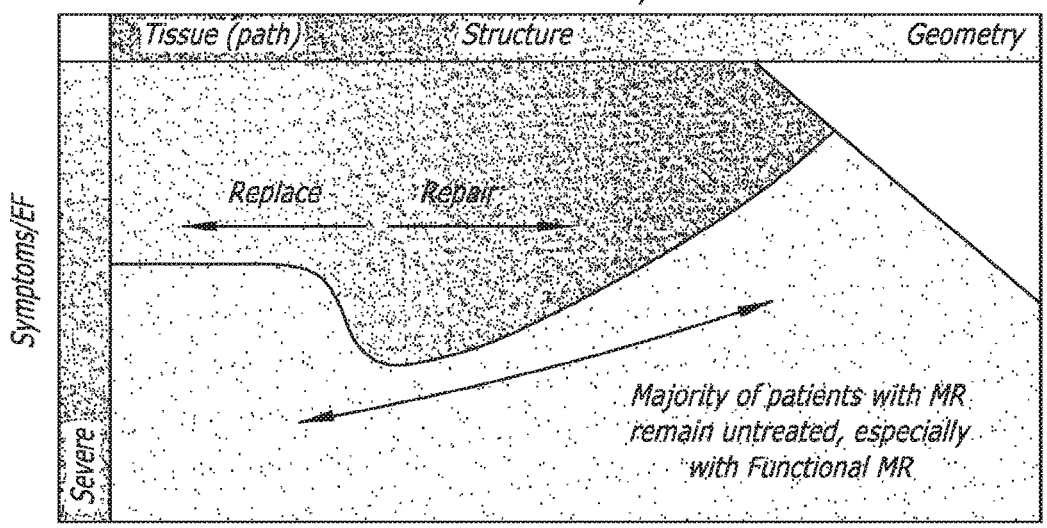
FIGS. 1A and 1B are graphical representations, depicting characteristics of potential patient populations.

Referring now to the drawings, which are provided by way of background and example, and not limitation, the present disclosure relates to medical interventional procedures and devices. In various aspects, heart valve repair is addressed and in particular, mitral valve reduction approaches are presented.

Figure 1B:
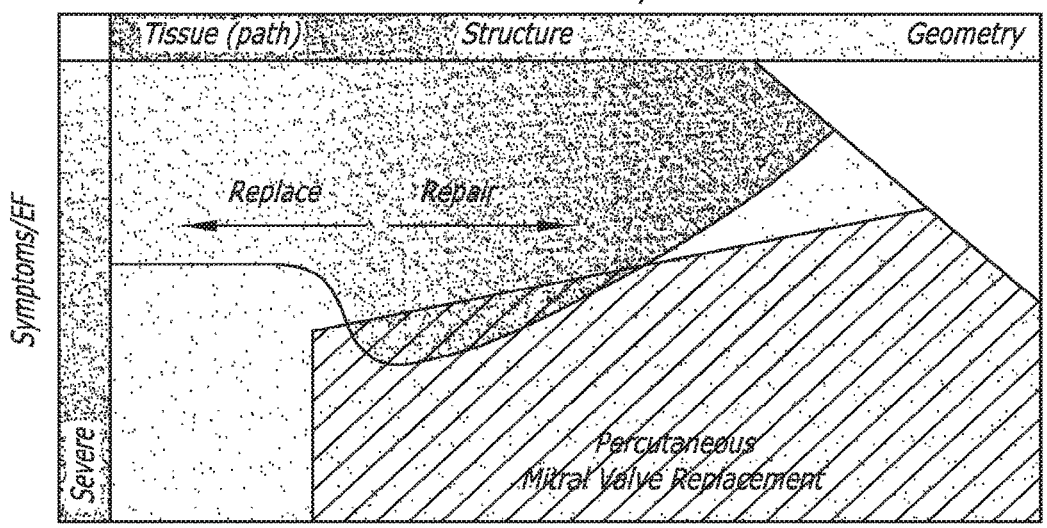

With reference to FIGS. 1A-B, there is shown a graphical representation of a potential patient population suffering from MR. Patents are classified by valve abnormality versus the severity of symptoms (i.e. ejection retraction). A decision to be made involves whether to replace or repair the subject valve. However, it has been found that a majority of patients with MR are left untreated. This is especially true with functional MR. It has been determined that such patients can be treated using a percutaneous mitral valve implant approach.

In open surgical valve replacement, the valve is implanted in its functional configuration and size. Additionally, conventional artificial surgical valves have a sewing ring around their perimeter that is directly attached to the valve annulus tissue with multiple sutures to provide both the securement and sealing functions. The surgical approach requires the heart to be stopped (cardiopulmonary bypass) and the atrium to be opened.

For less invasive, beating heart approaches to valve replacement, whether trans-apical access or endovascular access (venous/antegrade, arterial/retrograde), the valve is not in a functional configuration and is in a compressed state to aid deployment. This requires the valve to be deployed by some means to achieve its functional configuration and size. The requirements of sealing and anchoring the valve must also have a deployment mechanisms and/or structures. These procedural operations of deploying a functional valve, a tissue sealing structure, and a load bearing anchor structure that is solidly secured and sealed to the native anatomic location must be performed quickly and remotely to accommodate the desired less invasive and beating heart implantation. This combination of multiple deployable elements with multiple functional requirements of the composite system dramatically increases the complexity of the system and procedure.

In general, the most difficult of the three functions to reliably achieve can be the anchoring function due to the variable and cyclical load requirements and the complexity of the anatomic structures of the native mitral valve. The sealing function of the system is similarly difficult because of the pressure requirements and again, the complexity of the anatomic structures of the native mitral valve. The simplest is the deployable valve functional element, as the TAVI experience provides a basis for the starting point design structures and mechanisms.

It is desirable to have a simple and repeatable procedure to deliver a highly functional and long lasting valve system requires a different approach than currently being pursued by others in the field.

In order to accomplish this, the presently disclosed system contemplates a staged approach to the functional elements of the system, starting with the anchoring or securement functional element. Additionally, the staging can be performed within a single procedure or in multiple, time separated procedures. By staging and separating functional elements, the individual elements will be simpler in design and simpler to deploy and implant. This staging of the anchor implantation of the present invention provides a stable, reliable, consistent, substrate to deliver a replacement valve into the mitral position.

In current conventional approaches to valvular intervention, a diagnostic echocardiograph is initially performed to assess valve function followed by two percutaneous valve procedures. First, a diagnostic angiography is performed with or without a right heart catheterization to assess, for example, whether they might also require revascularization first, prior to intervention. Here, patients do not receive valve therapy without the patient being fully revascularized. Thereafter, at a different time and place, valve replacement therapy is performed involving fixation/attachment, accomplishing a tissue sealing interface, and valve deployment and then release. In contrast, the presently described approach, however, can include an assessment involving a diagnostic echocardiography followed by a unique percutaneous valve procedure sequencing. First, a diagnostic angiography (+/− right heart cath) can be performed along with anchor fixation/attachment and anchor/tissue sealing. Subsequently, either later or during the same interventional procedure, valve replacement therapy can occur involving valve deployment and release. Thus, since the anchor implant allows the native valve to remain functional, the anchor implantation procedure could be added to the end of the angio (+/−PCI) and not require a separate interventional procedure. A quick, simple, and reliable anchor deployment procedure could permit a fully ingrown structure that significantly enhances the holding force of a subsequently implanted replacement valve. Tissue ingrowth of the entire anchor perimeter or at key positions thereon can in fact provide the necessary tissue seal in advance of valve deployment. Moreover, the anchor design could be simplified due to less required acute holding force. Therefore, a tissue incorporated and healed anchor provides a structure to perform several methods of annular adjustment, including plication, reduction annuloplasty, and septal-lateral cinching.

Figure 2A:
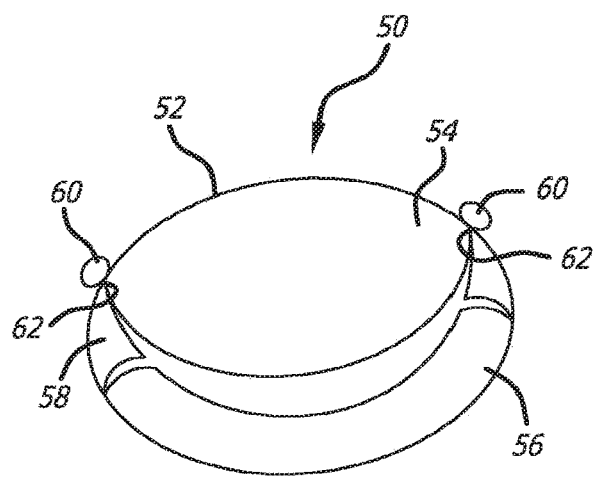
FIG. 2A is a schematic drawing of the mitral valve anatomy at the level of the mitral annulus.
Figure 2B:
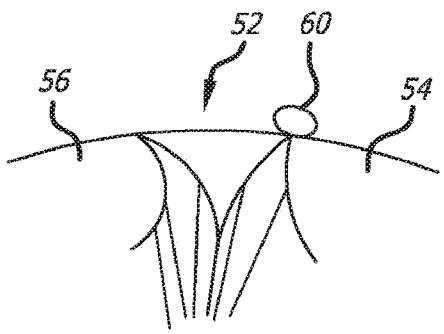
FIG. 2B is a side view, depicting a portion of the schematic from FIG. 2A.
Figure 2C:
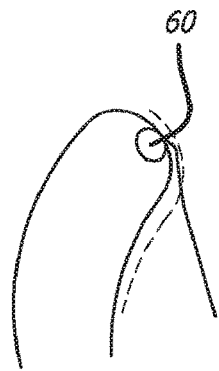
FIG. 2C is a schematic section view of the mitral commissural area, showing the region of possible anchor and/or anchor projection tissue engagement.
Figure 2D:
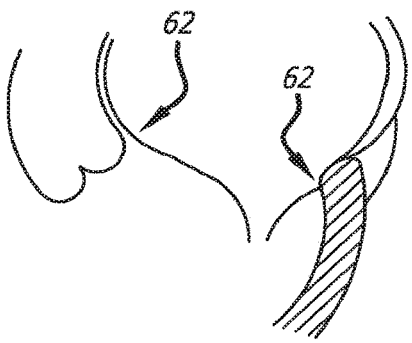
FIG. 2D is a vertical cross section through the aorta and the A2a/P2 segment of the mitral valve, depicting possible locations for attachment of the anchor to the valve tissue or anatomy.
Figure 2E:
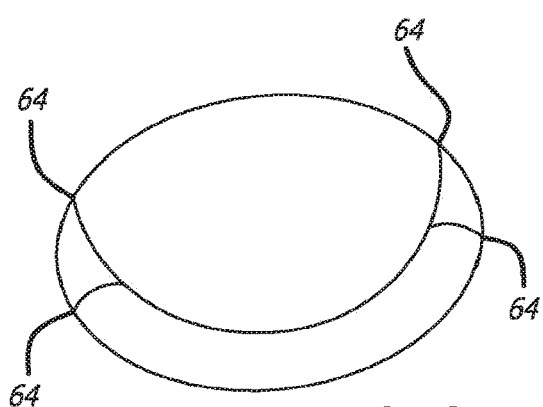
FIG. 2E is a transverse (short axis) cross section of the heart at the mitral valve annular level, depicting the commissural and posterior leaflet cleft locations as possible attachment locations for the anchor.

There are certain desirable anchoring locations for an anchor implant. Direct attachment to tissue is contemplated at locations adjacent the mitral valve, as are locations for placement of anchor projections at leaflet cleft locations. Again, it is intended that there be low or no impact to native leaflet function as a result of the implantation of an anchor implant so as to maintain the pre-existing native valve function until a replacement valve is implanted. At the mitral valve 50 (See FIGS. 2A-2E), there is of course the mitral annulus 52 defining structure from which the anterior leaflet 54 and posterior leaflet 56 extend and articulate. Between the anterior and posterior leaflets 54, 56 are commissural leaflets 58. The trigones 60 are positioned at a perimeter of the anterior leaflet 54 and adjacent the commissural leaflet 58. Commissures 62 are the openings or slits dividing the anterior leaflet 54 form the commissural leaflets, and positioned near the trigones 60. Such structure defines consistent and predictable anatomical features across patients. Notably, the high collagen annular trigone 60 generally can be relied upon to present a strong anchoring location. The muscle tissue in this area also provides a good ingrowth substrate for added stability. There is also a potential for sub-leaflet attachment for more stability (See FIG. 2C). Accordingly, primary anchoring locations 62, 64 for an anchor implant are included in FIGS. 2D and 2E.

Figure 3:
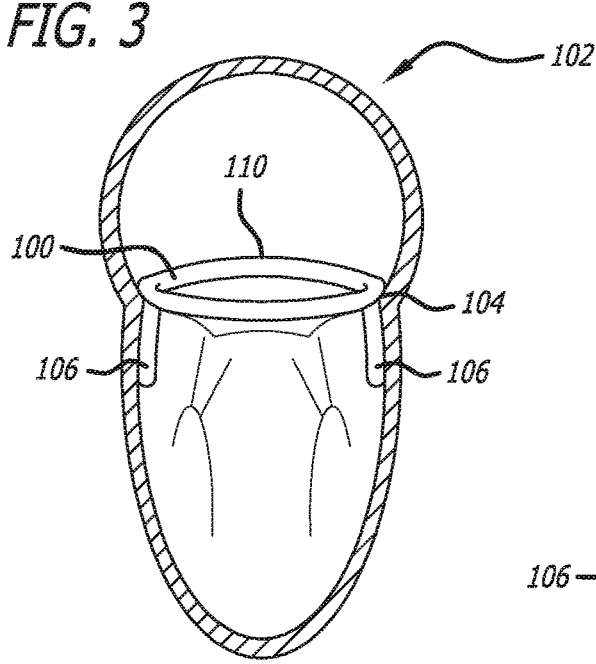
FIG. 3 is a vertical cross-section of the heart, depicting the posterior wall of LV with an exemplary anchor embodiment.
Figure 4:
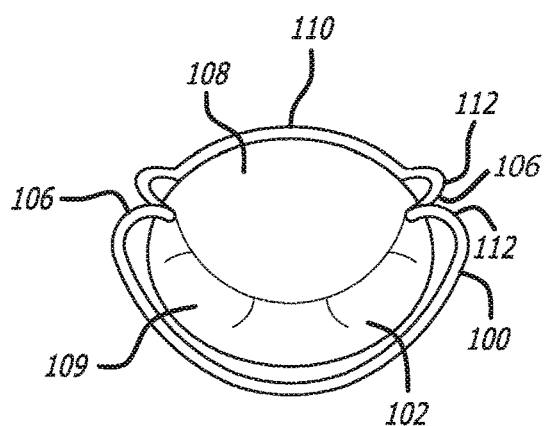
FIG. 4 is a transverse (short axis) cross section of the heart, depicting the mitral valve annular level of the exemplary embodiment of FIG. 1, showing the circular anchor structure.
Figure 5:
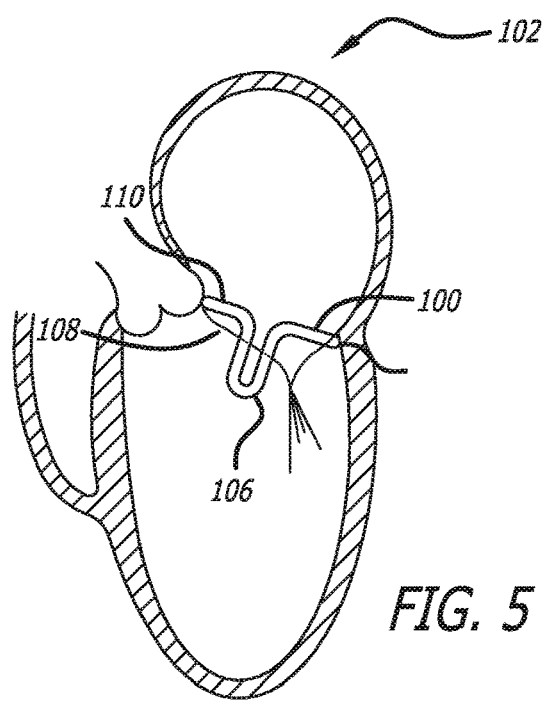
FIG. 5 is a vertical cross section through the aorta and the A2/P2 segment of the mitral valve, depicting the anchor of FIG. 1.

Turning now to FIGS. 3-5, there is shown one embodiment of an anchor implant 100 configured for atrial anchoring and implantation within the heart 102 at the mitral valve annulus 104. The anchor implant defines a supra-annular ring sized and shaped to be placed at the annulus, and includes commissural projections 106. As shown in FIG. 3, the projections 106 can be placed at an anterior commissural trigone 108. As described above, the commissural projections 106 are configured to extend between leaflets 109 without interfering with their functions (See FIG. 4). Moreover, as shown, the implant 100 includes a generally circular body 110 which can be formed from a wire or other structure, and the projections 106 are loops extending away from a plane defined by the circular body 110. It is to be further recognized that the body 110 includes a pair of bends 112 configured on opposite sides of the projections 106 to thereby provide necessary stress relief and clearance for the placement of the projections between leaflets 109. Furthermore as noted previously, the anchor 100 can be covered with various materials, such as PET and ePTFE, so as to present a desired biocompatible surface to body tissue.

Once the anchor is placed at a native valve, an artificial heart valve can then be implanted. Alternatively, it is contemplated that the artificial heart valve assembly can be implanted without the aid of an anchor, but rather includes its own anchoring substructure intended to secure the assembly in place.

One intention of mitral valve replacement is to maximize valve inflow area by implanting as large a valve as feasible to avoid stenosis or significant inflow gradients and to prevent the pulmonary and right-sided negative consequences of elevated left atrial pressures and possible pulmonary hypertension. Another consideration is to be able to implant a valve best suited for a particular patient (age, clinical status, etc.) or a particular valve pathology (functional MR, structural, mixed) without compromising the decision on valve size or type (tissue, mechanical). Another goal for percutaneous implantation is to be able to leverage the prior developments utilized in TAVI, specifically having a system that allows for both balloon expandable and self-expansion deployment mechanisms. When desired, the staging and separation of the implantation of a predictable and reliable anchor substrate disclosed herein provides for multiple options for an artificial valve structure. It is contemplated that the valve may include a structural frame or support component, a leaflet/occluder component, and an attachment feature or component.

In one approach, the valve structure may comprise a single valve. A stable and predictable, relatively circular and non-expandable anchor structure as disclosed herein is that it can secure a deployed circular valve without requiring a frictional fit between the anchor and valve, which can reduce the required radial hoop strength (collapse force) requirements of the valve frame. The interlock fit rather than an expanded frictional fit reduces the structural requirements of the valve, allowing the structural design to focus on valve performance loads rather than anchoring loads. The anchor structure may also allow for a larger surface area valve because of the separation of functions. If a single valve is utilized, it may consist of a traditional tri-leaflet construction with sufficient size (cross sectional area) to minimize flow restriction. To further maximize area and minimize leaflet stresses, more than 3 leaflets can be utilized.

In another approach, the valve structure may comprise dual or multiple valves. Implantation of dual parallel valves in the mitral orifice is an option as a means to achieve the desired cross sectional area of the valve while minimizing the loads and stresses of the individual artificial valves due to their smaller size. The substrate structure to receive the dual smaller circular artificial valves can be achieved either through an anchor that has a dual orifice planar configuration or via a separate interface implant that connects to a larger circular anchor ring but also has the dual orifice substrate.

In yet another approach, the valve structure may comprise dual series valves. The nature of a serial valve above the native allows for a reduction in impulse hemodynamic load of the artificial valve because the native valve is absorbing most of the immediate systolic forces. The artificial serial valve must be able to withstand the pressure times surface area forces during mid to late systole but does not need to withstand the immediate impulse force. This is important because it may allow for a reduction in the immediate anchoring load requirements of the system. This type of configuration also may allow for occlusion of the only the regurgitant volume of the native valve rather than the entire flow across the mitral orifice.

Moreover, in yet another aspect, the valve structure may comprise a valve within a valve. The nature of a valve in a valve is that the artificial valve only covers a fraction of the total valve area and therefore only encounters a fraction of the total anchoring forces required. Further, occluder designs and mechanisms may be utilized to provide valve function. These types of designs are constructed primarily from tissue or polymer constructs and rely on the valves geometry relative to the pressure and flow of the blood to occlude backward flow and distribute the load on the valve surfaces over a larger portion of the tissue.

One ability of the contemplated approaches is to implant a mechanical valve in a beating, functioning heart via a less invasive trans-apical or transatrial approach. Here, the mechanical valve can be attached or secured to anchor structure in a staged approach. During the procedure, the mechanical valve is attached around its annular perimeter to an introducer tool such that it can be tilted and rotated by the introducer during insertion and implantation. When tilted, the valve annular perimeter is in plane with the long axis of the introducer tool. The valve is inserted into the heart via a slit created in the atrium or LV wall of the heart. In order to create the slit while maintaining heart function, a portal device can be used and is constructed of a proximal hub/port, a collapsible oval or slit like tubular segment, and a distal segment that is attached to the heart via a purse string suture arrangement around its distal perimeter. This portal device serves as a vestibule like structure for sealed introduction of the valve and insertion tool. The distal end of the portal device is first attached to the atrial or ventricular wall via purse string sutures around the perimeter to create a blood tight seal. A slit is then created in the heart wall from within the portal device with the proximal hub preventing leakage or bleeding. The distal end of the tubular segment is then clamped while the valve and introducer distal end is inserted into the proximal segment of the portal tubular segment. The proximal hub/port is sealed around the introducer, air is evacuated and the distal clamp is then released allowing advancement of the flat planar valve and introducer structure through heart wall slit into the chamber. The valve is then further advanced, tilted, and rotated into position across the mitral valve and an engagement mechanism around the valve perimeter is used to engage and attach the mechanical valve to the anchor structure. Because a mechanical valve can be functional during deployment, no rapid pacing is anticipated during deployment. After valve deployment and insertion tool removal, the purse string sutures are tightened to seal the heart wall.

As stated, in general, the valve can consist of a support structure component and an occluder/leaflet component. The support structure can be the component or portion of the artificial valve that transfers loads from the occluder/leaflets to the anchor and/or tissue within the implant site. The support structure functions to hold the occluder/leaflets, transfer load into frame, and incorporates attachment components to attach to a previously placed anchor and/or tissue. The leaflet support component of the support structure attaches directly to the leaflets (sutures or alike) and supports and maintains the leaflet geometry as the valve opens and closes. The leaflet support component can be attached or be integral to the rest of the support structure. The attachment component of the support structure consists of a mechanism that allows stable and durable attachment of the support structure to the anchor. The attachment component interfaces with and transfers load to the anchor. There are several types of attachment methods contemplated. In one approach, there can be discrete connection points with mechanical fasteners consisting of small interlocking components. There can also be attachment components that provide broad geometric interlock between the support structure and anchor. These create a geometry that engages the anchor to provide a stable and durable attachment. Direct tissue attachment components could also be incorporated into the attachment component of the support structure. They would include barbs, hooks, as well as chronic ingrowth components such as mesh, porous, and velour materials. The support structure has similar requirements to other implanted components such as the anchor. For example, the support structure can be with tissue and blood, biostable (does not significantly degrade) corrosion resistant (resistant to general corrosion as well as fretting, galvanic, pitting, crevice, and stress corrosion), and durable/fatigue/resistant (function under the in vivo cyclically load conditions for the implant lifetime). Additionally, the support structure must be of sufficient mechanical strength to transfer the loads from the occluder/leaflets to the anchor, and be small enough to allow delivery though and catheter and minimize the amount of obstruction to blood flow after implantation.

As stated, the occluder/leaflet component is the component that prevents or inhibits backflow of blood from the left ventricle to the left atrium. One design requirement of an occluder/leaflet is durability. This is especially the case in the mitral position because of the high transvalvular pressure differentials. The leafletstake the load produced by the blood pressure gradient across the valve and transfers it to the support structure. Leaflets undergo large cycle displacements and therefore bend and fold repetitively. Occluder/leaftlets also repetitively interact with other valve structures, primary with other leaflets to create a seal (coaptation). This interaction creates wear and abrasion conditions which need to be addressed in the valve design. In order to enhance the durability of occluder/leaflet, minimizing stress within the leaflet, motion/strain of the leaflet and motion at contact areas with other structures (e.g. coaptation area) is required. Material selection can be critical to the durability and the function (flexibility). Geometry of the leaflets can minimize high local stresses and motion. Three leaflet configurations provide convenient geometric relationships in a circular configuration that help manage durability issues (stress and wear). Multiple leaflets provided smaller surface area per leaflet to occlude the same area. This reduces the stress and motion within an individual leaflet. Multiple independent valves can be used to accomplish the same objective.

Materials used to build the valve depend upon the intended valve function and structure. Metallic, tissue, and synthetic materials and combinations thereof may be used for the valves. Thus, metals may be used for the valve frame structures and can include Nitinol due to its superelasticity and ability to be compressed into a deliverable shape/state and then deployed into a functional state. Titanium can also be employed due to its strength and biocompatibility, or SST which is hardened for its strength or malleable to aid in conforming to shape. Moreover, a cobalt/chromium alloy is suitable for strength and a known valve component implant history, or composites can be used to provide multiple properties based on anatomic location. Further, tissue may be used for the occluder including pericardial (bovine, ovine, porcine) tissue or valve tissue (bovine, ovine, porcine), and synthetic polymers can be used as biocompatible elements in implants. In this regard, Elast-Eon (a silicone and urethane copolymer), ePTFE, Urethane, Silicone, PEEK, and/or Polyester (PET) can be used as well as UHMWP.

Figure 6:
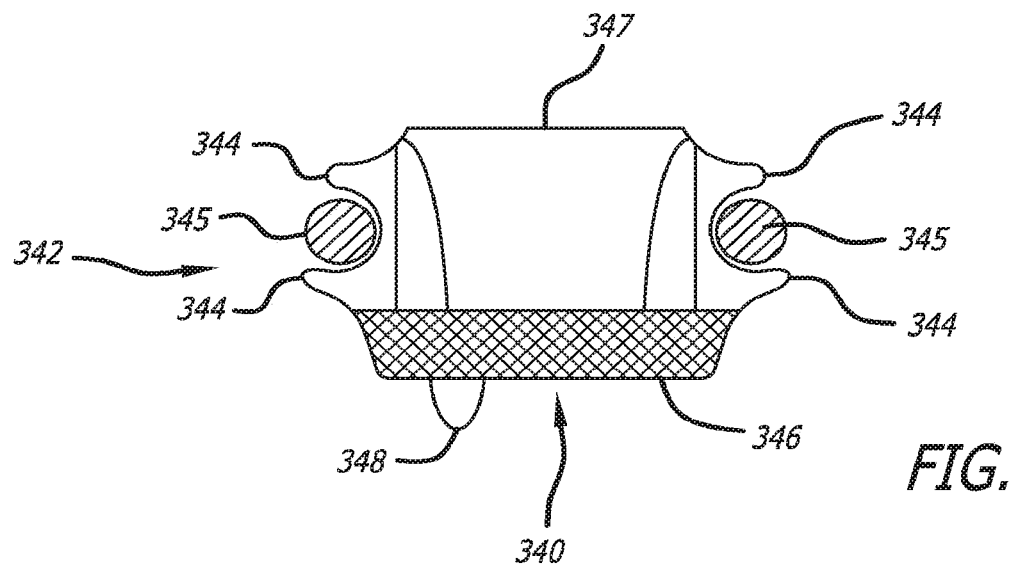
FIG. 6 is a cross-sectional view, depicting an exemplary embodiment of a tri-leaflet artificial valve and anchor structure according to the present teachings.
Figure 7:
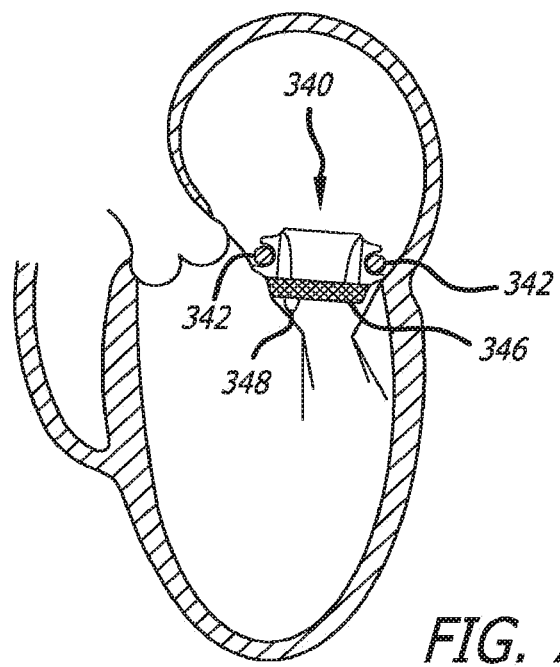
FIG. 7 is a vertical cross section through the aorta and the A2/P2 segment of the mitral valve, depicting tri-leaflet deployable artificial valve and exemplary anchor structure/substrate of FIG. 6.

Turning now to the figures, there are presented various contemplated approaches to valve assemblies. Although described in context with the mitral valve, such structure can also be adapted for other heart valves. In one approach (FIGS. 6-7), a valve assembly 340 sized and shaped to engage anatomy at a native mitral valve can include a geometric locking structure 342 for facilitating a secure implantation at a mitral valve annulus. It is intended that the valve to native valve interface preserves subvalvular structural relationships. Thus, the device can be provided with annular ridges 344 sized and shaped to lockingly receive an anchor implant 345 such as that described above and which was previously placed within the interventional site. Moreover, it is to be recognized that valve assemblies disclosed herein can be configured to engage one or more of the anchor structures depicted in copending U.S. application Ser. No. 13/842,206, the contents of which are incorporated herein by reference. A downstream portion of the valve assembly 340 can include a tapered portion 346 contoured to mate with native mitral valve anatomy. The tapered portion 346 can be further equipped with a tissue engaging or ingrowth surface such as a woven structure which extends from a generally cylindrical upper section 347. A downwardly projecting member 348 is further provided to stabilize the valve assembly 340 in place against rotational forces.

Figure 8:
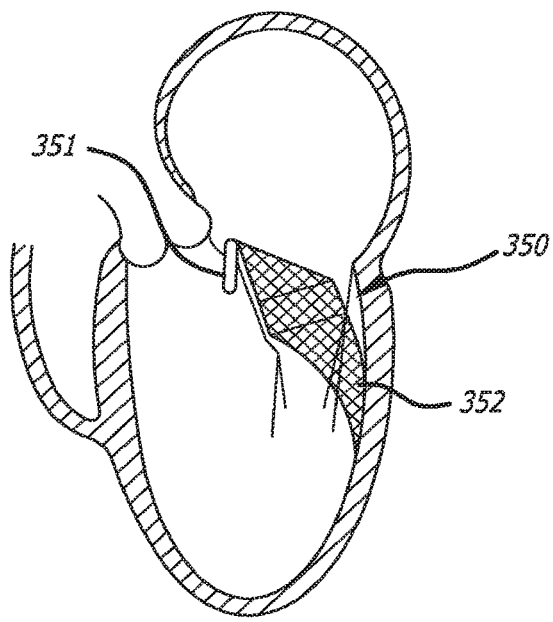
FIG. 8 is a vertical cross section through the aorta and the A2/P2 segment of the mitral valve, depicting an alternative exemplary embodiment of an artificial valve.
Figure 9:
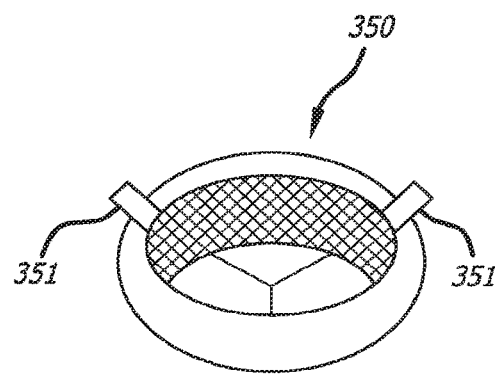
FIG. 9 is a top view of the valve of FIG. 8.
Figure 10:
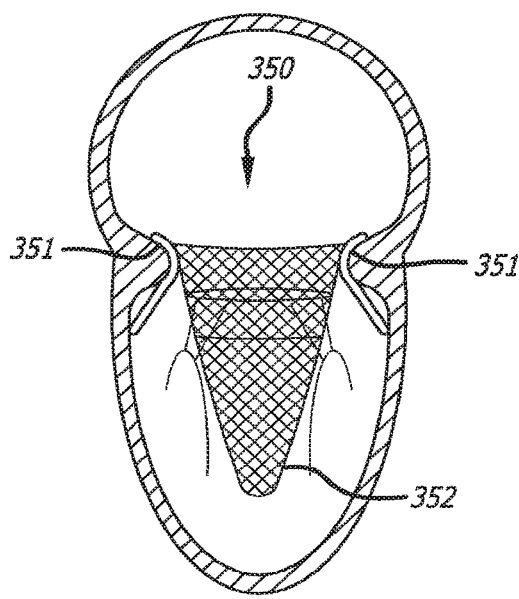
FIG. 10 is a vertical cross-section of the heart looking at the posterior wall of LV, depicting the valve of FIG. 8.

As shown in FIGS. 8-10, it is also contemplated that a valve assembly 350 can include structure adapted for placing the assembly at an angle across a native valve opening to be better responsive to pressure loads within the heart. Here, a loading vector with a posterior wall of the heart and anterior annulus anchor 351 can be improved by providing the valve assembly with a tapered section 352 which extends within and engages an internal wall of the LV. Thus, at its upper end, the valve assembly 350 securely engages the anchor implant 351 and at its lower extremity, the tapered portion 352 is supported by the LV, either with acute fixation elements such as anchors into the LV wall, or with tissue ingrowth into the tapered portion 352, or both. With this arrangement, the valve assembly presents an angled profile suited to be responsive to loading within the native valve structure. In one approach, valve assembly 350 leaflets are angled with respect to native valve leaflets.

Figure 11:
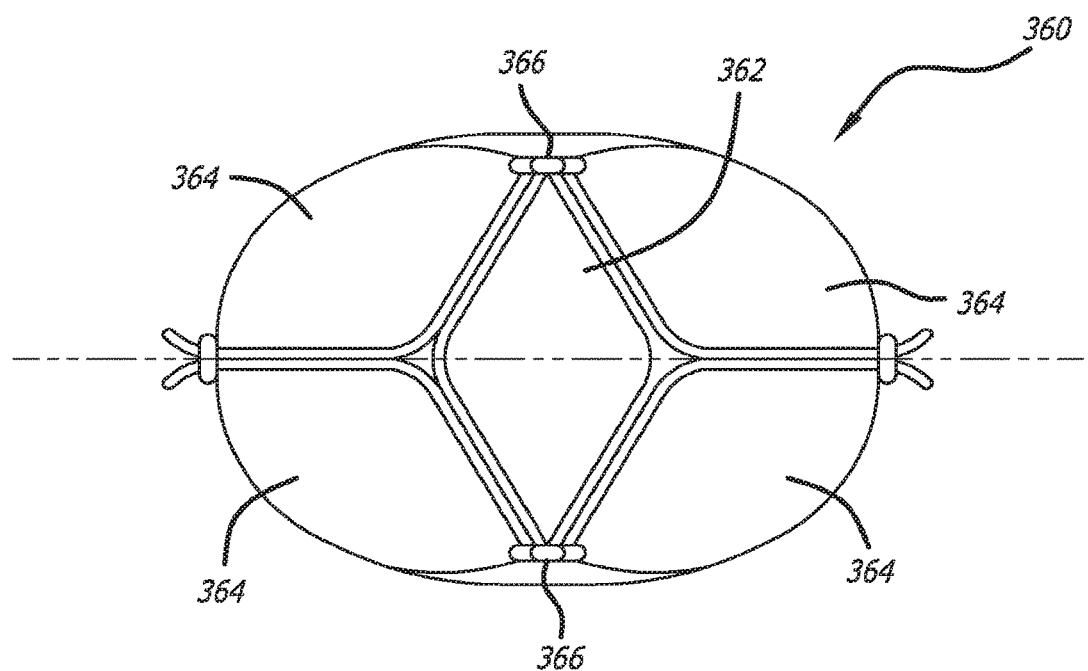
FIG. 11 is a view from the ventricular side of an exemplary embodiment of a five-leaflet mitral valve, depicting an envelope center leaflet.
Figure 12:
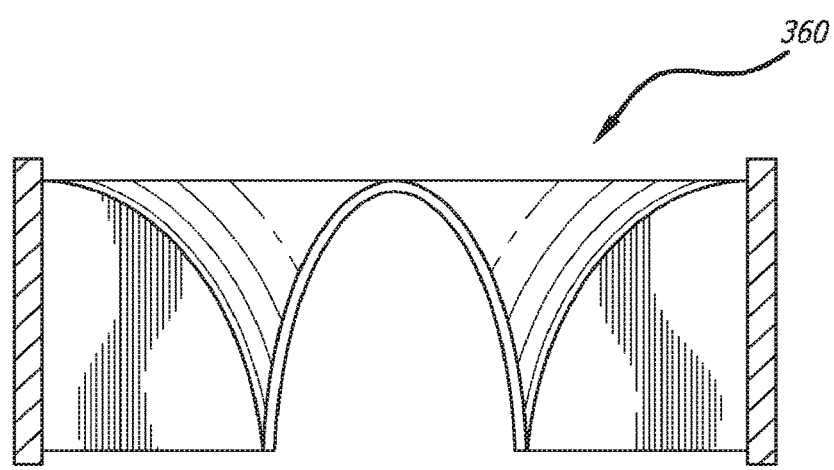
FIG. 12 is a sectional view, the five-leaflet valve of FIG. 11.

It has further been contemplated that various different multi-leaflet valve approaches may be best suited for particular patients or applications. With reference to FIGS. 11 and 12, a five leaflet valve assembly 360 is presented. An envelope center valve 362 is bounded by four separate peripheral 120° degree valve leaflets 364. The envelope center valve 362 is attached at opposite ends to an outer valve frame 366 and folds along a center line. The center valve outer edges meet the edges of the peripheral leaflets 364 to close the valve assembly. Adjacent peripheral leaflets also engage each other when the valve assembly 360 is closed.

Figure 13:
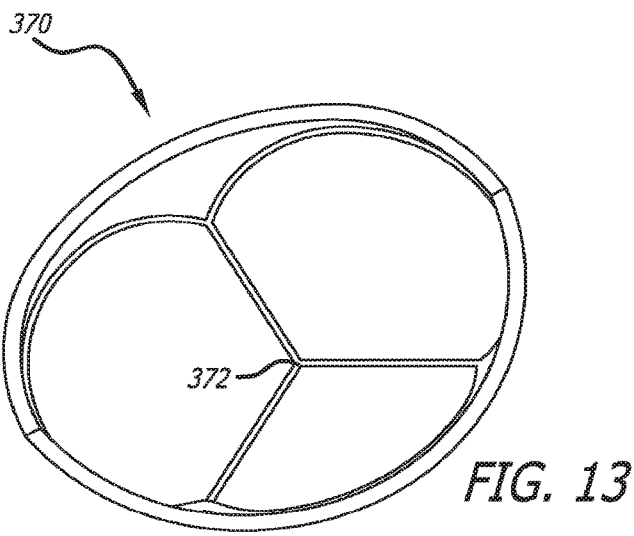
FIG. 13 is a top view, depicting a multi-leaflet valve frame that includes a central triangular leaflet strut frame.
Figure 14:
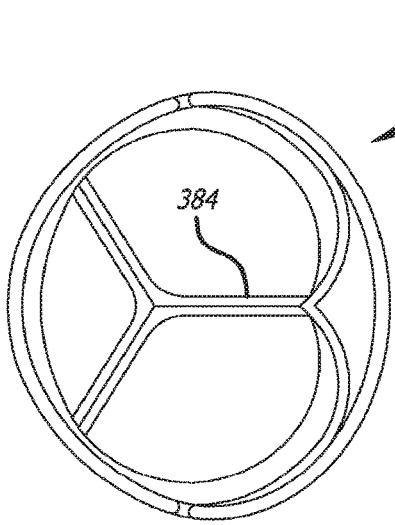
FIG. 14 is another embodiment of a multi-leaflet valve assembly using the frame of FIG. 13 in an open configuration.
Figure 15:
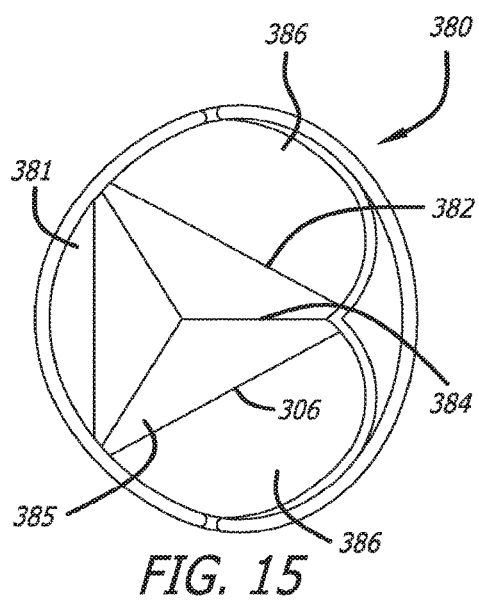
FIG. 15 depicts a closed configuration of the valve assembly of FIG. 14.
Figure 16:
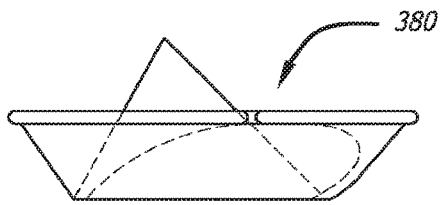
FIG. 16 is a side view, depicting the valve assembly of FIG. 14.
Figure 17:
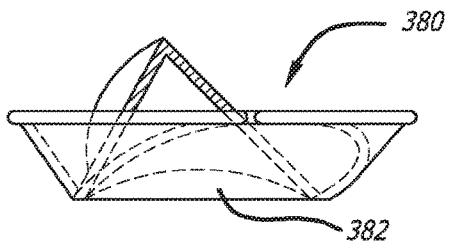
FIG. 17 is a side view, depicting the valve assembly of FIG. 15.
Figure 18:
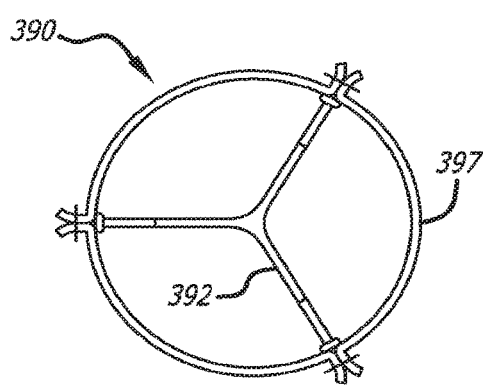
FIG. 18 is a top view, depicting another embodiment of a multi-leaflet valve.
Figure 19:
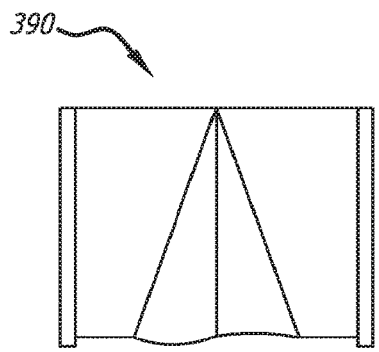
FIG. 19 is a sectional view of the valve assembly of FIG. 18.
Figure 20:
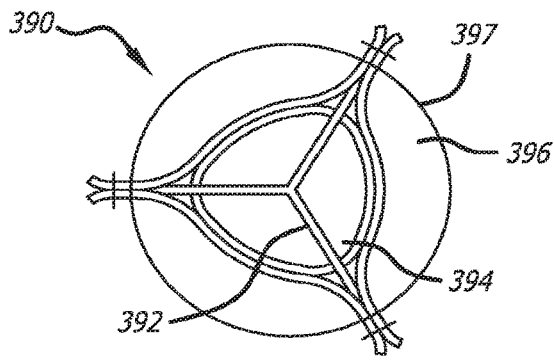
FIG. 20 is a top view, depicting the multi-leaflet valve of FIG. 18.
Figure 21:
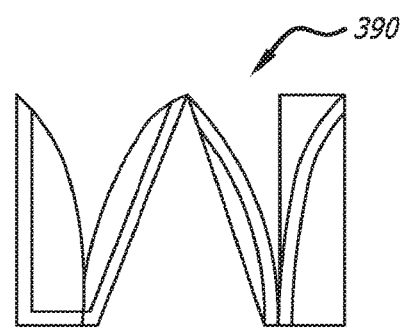
FIG. 21 is a sectional view, depicting the valve assembly of FIG. 20.

In FIG. 13, there is shown a valve assembly 370 including a multi-leaflet valve frame including a central three piece crossing strut frame 372 from which individual leaflets can articulate. In one approach to a valve assembly employing the strut frame (FIGS. 14-17), a fabric covered valve assembly 380 can include a triangular coaptation zone 382. The central strut frame 384 supports three centrally located leaflets 385 which are surrounded by a generally B-shaped second frame 386, the same supporting an additional three outer leaflets 386, inner borders of which being configured to meet outer borders of the central leaflets 385 to define the triangular coaptation zone 382. It is noted that in this particular approach, two of the outer leaflets have a generally mirror image, while the third outer leaflet has a much narrower profile.

In yet another valve assembly 390 including a central strut frame 392 (FIGS. 18-21), there are four leaflets, a single internal leaflet 394 supported by the center frame 392, bounded by three external leaflets 396 having general sizes and shapes. A second frame 397 which engages the internal frame has a generally circular shape. Coaptation occurs between external edges of the internal leaflet 394 which folds into three sections when opened, with the internal edges of the external leaflets 396. Along an outer section of each arm of the internal center frame 392 towards the outer frame 397, portions of the adjacent outer leaflets 396 engage in a coaptation.

Figure 22:
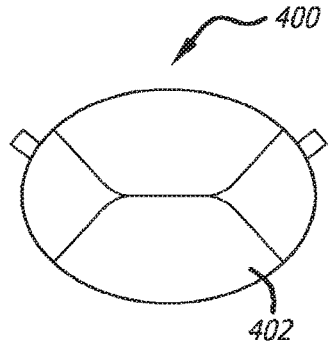
FIG. 22 is a transverse sectional view, depicting an embodiment of a four-leaflet valve.
Figure 23:
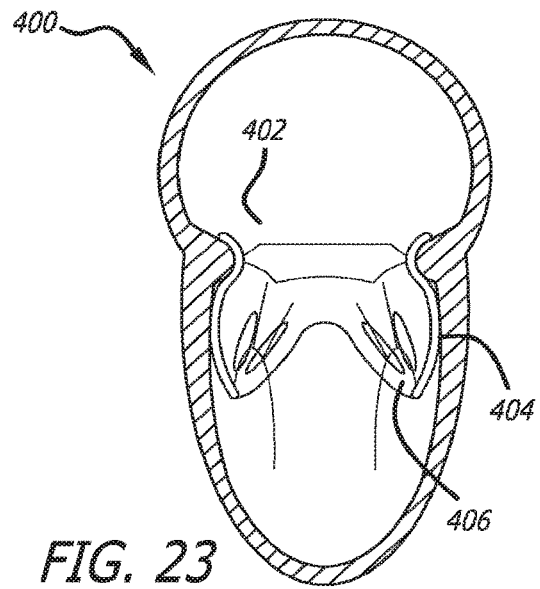
FIG. 23 is a sectional view of the left ventricle, depicting the valve of FIG. 22.
Figure 24:
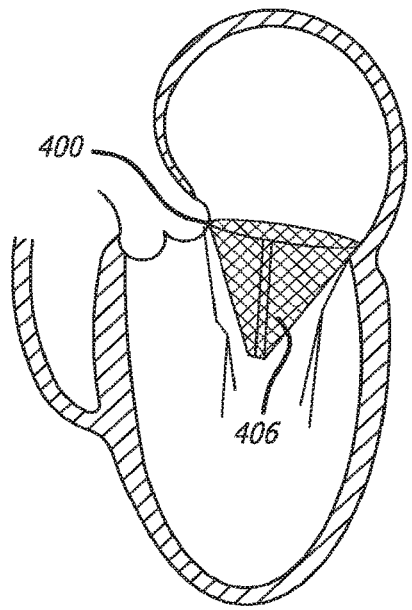
FIG. 24 is a vertical cross section through the aorta and the A2/P2 segment of the mitral valve, depicting a view of the valve in FIG. 22.

With reference to FIGS. 22-24, there is shown a valve assembly 400 having four heavily redundant leaflets 402. This assembly further includes a commissural anchor structure having feet projections 404 extending down into the LV, where non-coaptive tips 406 of the leaflets attach. Such attachment within the LV is beyond and/or displaced from native valve sub structure.

Figure 25:
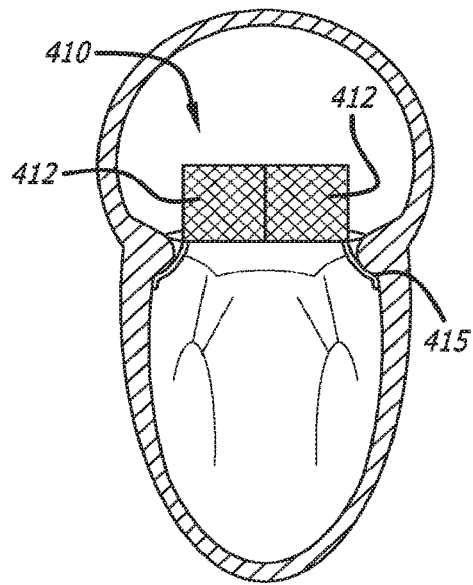
FIG. 25 is a vertical cross-section of the heart looking at the posterior wall of LV, depicting an embodiment utilizing dual replacement valves.
Figure 26:
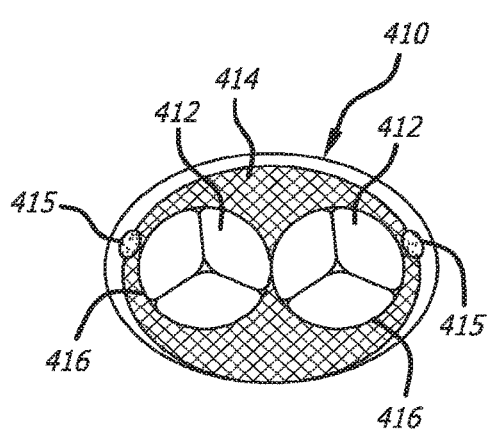
FIG. 26 is a transverse section, depicting the dual valves of FIG. 25.
Figure 27:
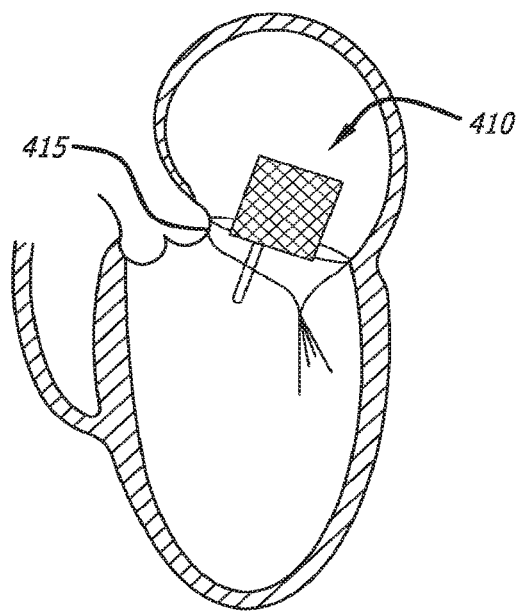
FIG. 27 is a vertical cross sectional view of through the aorta and the A2/P2 segment of the mitral valve, depicting the valve of FIGS. 25 and 26.
Figure 28:
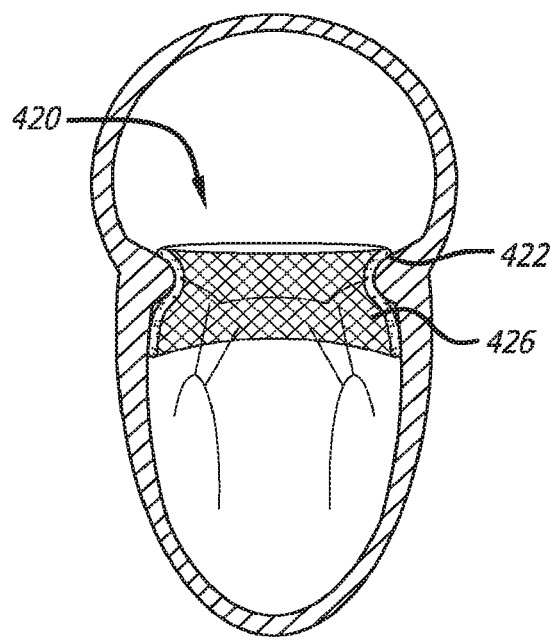
FIG. 28 is a vertical cross-section of the heart looking at the posterior wall of LV, depicting an embodiment of a valve in a native valve.
Figure 29:
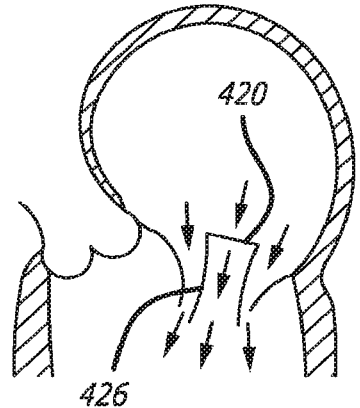
FIG. 29 is a vertical cross section through the aorta and the A2/P2 segment of the mitral valve, depicting the valve of FIG. 28.
Figure 30:
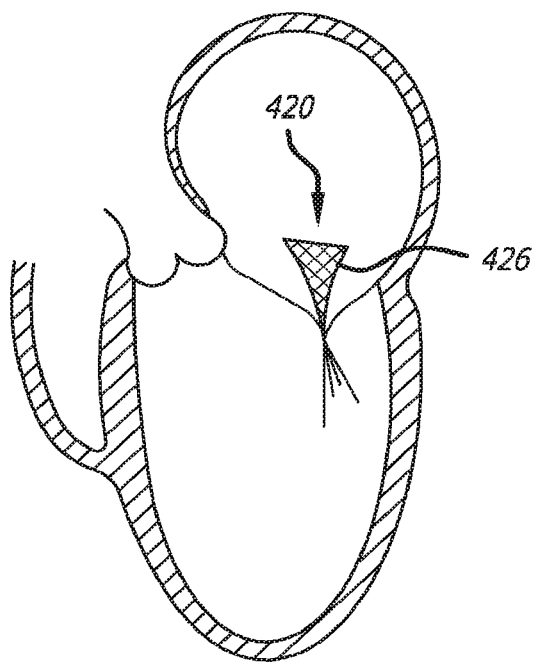
FIG. 30 is a vertical cross section through the aorta and the A2/P2 segment of the mitral valve, depicting the valve of FIG. 28.
Figure 31:
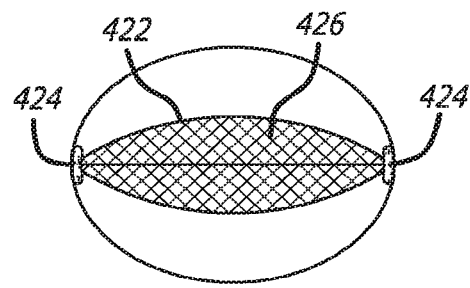
FIG. 31 is a transverse top view at the mitral annulus level of FIG. 28.

In an alternative approach (FIGS. 25-27), a dual valve assembly 410 is contemplated. Accordingly, the assembly 410 can include two tri-leaflet valves 412 arranged side-by-side within a generally oval shaped skirt frame 414 covered with a wire mesh fabric. The frame 414 is sized and shaped to securely engage or include anchors 415 configured through valve commissures. A pair of adjacent internal circular frames 416 are further provided to support the tri-leaflet valves 412.

A valve assembly can alternatively include structure that is responsive to action of the native valve. As shown in FIGS. 28-31, a valve assembly 420 suspended within the coaptation line of a native valve can include a generally oval, narrow frame 422 sized to extend across a native valve opening. Opposite long ends 424 can be configured to engage an anchor implant 425 placed at the native valve, or can include projections engaging the LV walls itself. Longitudinally extending valve leaflets 426 are open (FIG. 29) when the native leaflets are open, and close (FIG. 31) in response to the closure of native leaflets. The valve is intended to be anchored in valve commissures and/or to the trigone.

Figure 32:
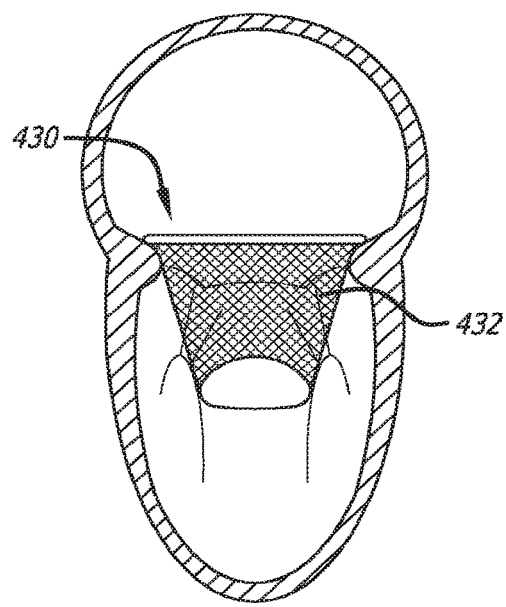
FIG. 32 is a vertical cross-section of the heart looking at the posterior wall of LV, depicting an embodiment of a tubular valve.
Figure 33:
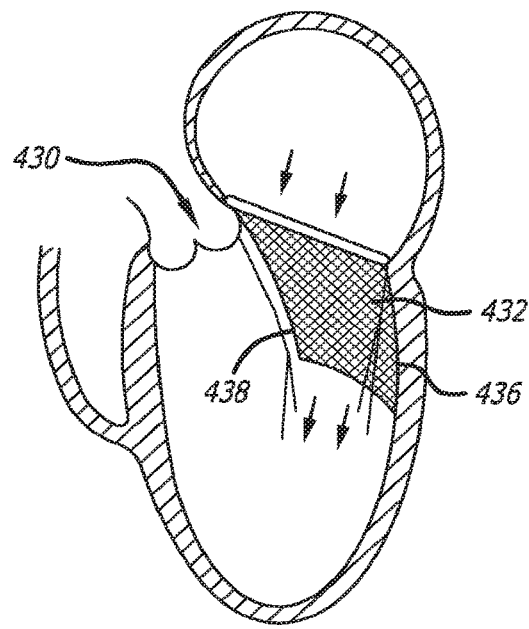
FIG. 33 is a vertical cross section through the aorta and the A2/P2 segment of the mitral valve, depicting the valve of FIG. 32.
Figure 34:
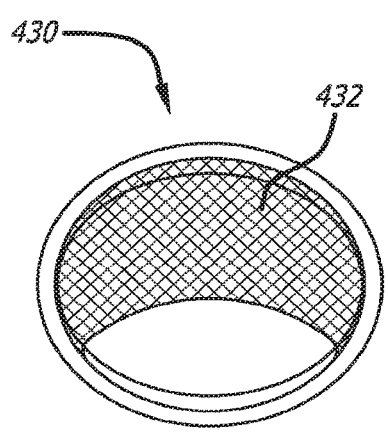
FIG. 34 is a transverse cross section at the mitral annulus level with a top view of the valve of FIG. 32.
Figure 35:
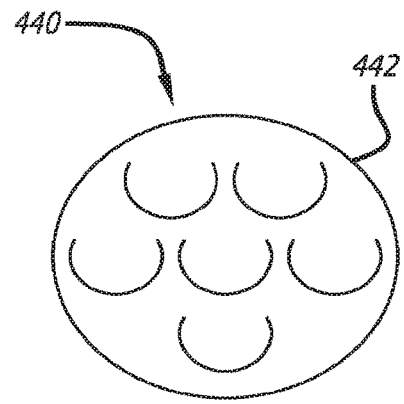
FIG. 35 is a top view, depicting an embodiment of a planar valve concept.
Figure 36:
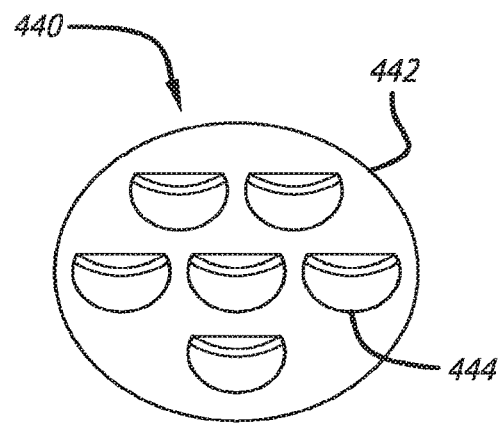
FIG. 36 is a top view of the planar valve concept of FIG. 35.
Figure 37:
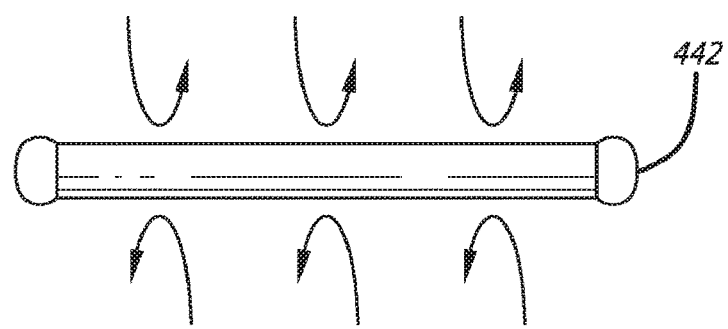
FIG. 37 is a side view of the valve of FIG. 35.
Figure 38:
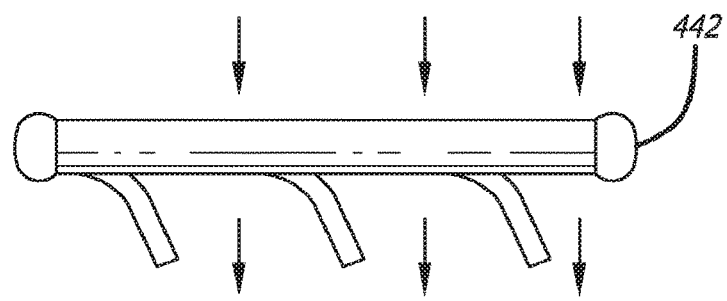
FIG. 38 is a side view of the valve of FIG. 36.

As shown in FIGS. 32-34, a valve implant 430 can also embody a tubular body structure 432. A ring-like frame 434 defines an opening to the valve 430, and extending downwardly from the frame is the tubular body 432. A lateral section 436 of the tubular body 432 can be configured to supportively engage or be mated to the LV wall. The assembly also includes an opposite lateral wall 438 defining collapsible structure which is closeable to prevent flow.

A valve assembly 440 can further include a frame 442 supporting a plurality of multiple slot or flap-like leaflets 444 formed in a surface extending across the frame 447 (See FIGS. 35-38). Each of the leaflets can be arranged in similar directions as shown in the figures, or can be arranged to present varyingly arranged openings, to thereby open and close to control blood flow.

Further modifications and alternative embodiments will be apparent to those of ordinary skill in the art in view of the disclosure herein. For example, the systems and the methods may include additional components or steps that were omitted from the diagrams and description for clarity of operation. Moreover, those of ordinary skill in the art will appreciate that aspects and/or features disclosed with respect to one embodiment in some case may be incorporated in other embodiments even if not specifically described with respect to such other embodiments. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. Accordingly, this description is to be construed as illustrative only and is for the purpose of enabling those skilled in the art the general manner of carrying out the present teachings. It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

Thus, it will be apparent from the foregoing that, while particular forms of the invention have been illustrated and described, various modifications can be made without parting from the spirit and scope of the invention.

We claim:

1. A mitral heart valve assembly system co configured for staged implantation at a native mitral valve site via an endovascular access to a heart, comprising:

an anchor assembly to implant along a native mitral valve annulus while maintaining pre-existing native valve function, the anchor assembly including: a supra-annular structure defining a first mating face at an upper portion of the anchor assembly configured to reside above the valve annulus of the native mitral valve; a plurality of wire structures that extend downwardly away from the supra-annular structure and are sized and shaped to extend through commissures between the native mitral valve leaflets and into a sub-annular position; and a plurality of sub-annular anchor projections connected to the wire structures and being sized and shaped to anchor into a sub-annular gutter along an underside of the valve annulus of the native mitral valve; and a valve assembly configured to subsequently mate with the anchor assembly after implantation of the anchor assembly, wherein the valve assembly includes: an occluder component having a plurality of leaflets positioned to occlude blood flow during systole and open to blood flow during diastole; a support component to maintain a portion of the occluder component in a supra-annular position above the valve annulus of the native mitral valve and further having a second mating face sized and shaped to be positioned inwardly of and directly mate with the first mating face of the supra-annular structure of the anchor assembly; and a lower peripheral portion that is sized and shaped to extend below the valve annulus of the native mitral valve while the support component maintains the portion of the occluder component in the supra-annular position above the valve annulus.

2. The system of claim 1, wherein the occluder component of the valve assembly comprises a tri-leaflet construction in which said plurality of leaflets comprise three centrally located leaflets together define a generally circular periphery when in a closed position.

3. The system of claim 2, wherein the plurality of leaflets are formed from pericardial tissue.

4. The system of claim 1, wherein the anchor assembly is configured to seat along the native mitral valve annulus while the plurality of wire structures extend between the native mitral valve leaflets to maintain pre-existing native valve function.

5. The system of claim 4, wherein the sub-annular anchor projections include loop structures that are shaped to anchor along the native heart tissue below the valve annulus of the native mitral valve.

6. The system of claim 5, wherein two of the sub-annular anchor projections have the loop structures that are shaped to anchor proximate to trigones along the native heart tissue of the native mitral valve without interfering with the functionality of native mitral valve leaflets.

7. The system of claim 6, wherein at least a portion of the anchor assembly is covered with ePTFE material.

8. The system of claim 1, wherein valve assembly includes attachment components extending from the support component to mechanically fasten with the anchor assembly.

9. The system of claim 8, wherein the attachment components of the valve assembly extend from the support component to mechanically fasten with a portion of the anchor assembly above the native mitral valve annulus.

10. The system of claim 9, wherein the valve assembly comprises a Nitinol frame and pericardial tissue material.

11. The system of claim 1, wherein the valve assembly is configured to geometrically interlock with the anchor assembly while preserving subvalvular structural relationships.

12. The system of claim 11, wherein the valve assembly is adjustable from a compressed state during the staged implantation to a deployed state in the heart.

13. The system of claim 12, wherein the anchor assembly is configured to seat along the native mitral valve annulus while the plurality of wire structures extend between the native mitral valve leaflets to maintain pre-existing native valve function.

14. The system of claim 13, wherein the sub-annular anchor projections include loop structures that are shaped to anchor along the native heart tissue below the valve annulus of the native mitral valve.

15. The system of claim 14, wherein two of the sub-annular anchor projections have the loop structures that are shaped to anchor proximate to trigones along the native heart tissue of the native mitral valve without interfering with the functionality of native mitral valve leaflets.

16. The system of claim 15, wherein at least a portion of the anchor assembly is covered with ePTFE material.

17. The system of claim 16, wherein the lower peripheral portion of the valve assembly comprises a lower contoured peripheral wall configured to engage with the native mitral valve, wherein at least a portion of the lower contoured peripheral wall is tapered inwardly.

18. The system of claim 17, the valve assembly further comprising a generally cylindrical portion and the lower contoured peripheral wall extending from the generally cylindrical portion.

19. The system of claim 1, wherein the lower peripheral portion of the valve assembly comprises a lower contoured peripheral wall configured to engage with the native mitral valve, wherein at least a portion of the lower contoured peripheral wall is tapered inwardly.

20. The system of claim 19, the valve assembly further comprising a generally cylindrical portion and the lower contoured peripheral wall extending from the generally cylindrical portion.

* * * * *